(12) United States Patent
Shimoda et al.

(10) Patent No.: US 8,017,162 B2
(45) Date of Patent: Sep. 13, 2011

(54) ANTI-INFLAMMATORY AGENT

(75) Inventors: Hiroshi Shimoda, Aichi (JP); Shaojie Shan, Aichi (JP); Junji Tanaka, Aichi (JP); Tadashi Okada, Aichi (JP); Hiromichi Murai, Aichi (JP)

(73) Assignee: Oryza Oil & Fat Chemical Co., Ltd., Aichi (JP)

( * ) Notice: Subject to any disclaimer, the term of this patent is extended or adjusted under 35 U.S.C. 154(b) by 94 days.

(21) Appl. No.: 11/585,819

(22) Filed: Oct. 25, 2006

(65) Prior Publication Data

US 2007/0154575 A1 Jul. 5, 2007

(30) Foreign Application Priority Data

Oct. 26, 2005 (JP) ................................ 2005-311848
Jan. 12, 2006 (JP) ................................ 2006-005421

(51) Int. Cl.
*A61K 36/906* (2006.01)
*A61K 31/70* (2006.01)
(52) U.S. Cl. ........................................ 424/756; 514/62
(58) Field of Classification Search ........................ None
See application file for complete search history.

(56) References Cited

U.S. PATENT DOCUMENTS

| 6,534,086 | B1 * | 3/2003 | Krumhar | ........................ 424/464 |
| 6,713,096 | B2 * | 3/2004 | Cho | .............................. 424/756 |
| 2003/0035853 | A1 * | 2/2003 | Weidner | ........................ 424/756 |

FOREIGN PATENT DOCUMENTS

| EP | 0 265 858 | * | 5/1988 |
| JP | 2001-247602 | | 9/2001 |

OTHER PUBLICATIONS

Hou et al.: Molecular Mechanisms Behind the Chemopreventive Effects of Anthocyanidins.: Journal of Biomedicine and Biotechnology.: 2004. 321-325.*
"Food". retrieved from the internet. Dec. 4, 2003. <http://web.archive.org/web/20031204142314/http://en.wikipedia.org/wiki/Food>. Retrieved on May 27, 2009.*

* cited by examiner

*Primary Examiner* — Melenie McCormick
(74) *Attorney, Agent, or Firm* — Clark & Brody

(57) ABSTRACT

This invention provides an anti-inflammatory agent or the like which is safer and less adverse and has the great effectiveness to prevent and treat arthritis, or the like. An anti-inflammatory agent or the like in this invention is characterized by comprising anthocyanidin and gingerol as an active substance. Also, the abovementioned anthocyanidin and gingerol are preferably extracted from red ginger.

5 Claims, 6 Drawing Sheets n=12, Average value ± Standard error; *P<0.05; **PP<0.01 n=12, Average value ± Standard error, *P<0.05

Concentration of red ginger extract (μg/mL)

Effect of the glucosamine hydrochloride on NO production in RAW264.7 cells

ANTI-INFLAMMATORY AGENT

This invention relates to an anti-inflammatory agent to prevent or treat arthritis or the like.

BACKGROUND OF INVENTION

Arthrosis of mammals including human beings is always in danger of being easily inflamed or physically broken from mechanical stimulus caused by daily body movements or exercise. Factors of damage in the arthrosis (hereinafter referred to as "Articular Disorder") are contagion, external injuries, allergies, abnormal metabolic processes, obesity, blood circulation disorders or the like. It has been pointed out that Articular Disorder rates increase with advancing age. Articular Disorder is becoming one of the more serious social problems among Japan's recent aging population.

Articular Disorder generally is accompanied by inflammation. Therefore, many cases of A.D. are now treated with an anti-inflammatory agent.

DISCLOSURE OF INVENTION

Problems to be Resolved by the Invention

In such circumstances described above, the inventors researched and found that anthocyanidin, gingerol and the like have an effect to prevent or treat Articular Disorder. And they also learned in the research that the anti-inflammatory agent, comprising of both anthocyanidin and gingerol, can easily be produced by using red ginger (*Zingiber officinale* Roxb.) which contains anthocyanidin and gingerol.

This invention provides an anti-inflammatory agent which is safer and less adverse and has the great effectiveness to prevent and treat arthritis, or the like. Furthermore, the anti-inflammatory agent can be very easily manufactured by a many natural substances which are derived from a single species of plant.

Means of Solving the Problems

To resolve the above problems, an anti-inflammatory agent in this invention is characterized by comprising the following properties.

A composition comprising a red ginger extract effective to inhibit the inflammation.

PREFERRED EMBODIMENTS

This invention is described below.

The aforementioned composition or anti-inflammatory agent, as well as the prophylactic agent for arthritis, the therapeutic agent for arthritis, the prophylactic agent for rheumatism, the therapeutic agent for rheumatism, the antipyretic agent and the analgesic agent (hereinafter referred to as "anti-inflammatory agent or the like") comprising the anti-inflammatory agent in this invention, are all characterized by comprising anthocyanidin and gingerol.

Gingerol is indicated below by the chemical formula (1). Gingerol in this invention includes 6-gingerol, 8-gingerol, 10-gingerol, 12-gingerol and others. Only one gingerol can be used. And two or more gingerols can also be used together. It is preferable that at least 6-gingerol be used. As for the 6-gingerol, "n" should be 4 (n=4) in the chemical formula below.

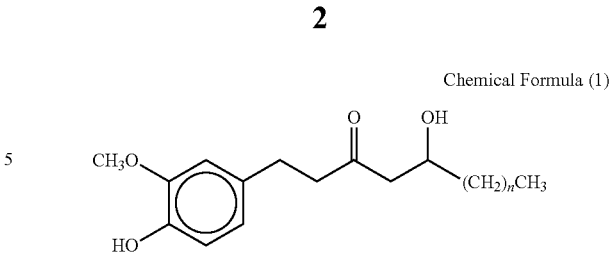

Chemical Formula (1)

There are two different methods to obtain the gingerol: one is a synthesis approach and the other is a plant extraction method. The plant extraction method is preferably used. Also, the ingredient used can be ginger (Zingiberaceae), red ginger (*Zingiber officinale* Roxb.), or the like. However, red ginger is preferably used in this invention. As will be described later, red ginger contains anthocyanidin. Therefore, both anthocyanidin and gingerol can be obtained from red ginger.

Anthocyanidin is a generic term of chemical compounds comprising flavilium as a basic skeleton and includes anthocyanin, proanthocyanidin or the like.

Anthocyanin is a glycoside of the aforementioned anthocyanidins, including but not limited to anthocyanin 1, heavenly blue anthocyanin, anthocyanin B, delphinidin, cyanidin, petunidin, peonidin, malvidin or the like. Only one anthocyanin can be used. However, two or more can also be used.

Proanthocyanidin is a group of compounds consisting of condensation polymerization with polymerization grade 2 or more in which the constituent units are flavan-3-ol and/or flavan-3,4-diol.

Also, at least anthocyanin is preferably contained.

To obtain anthocyanidin, the ingredients, red ginger, red cabbage, purple sweet potato, purple corn, red radish, red perilla, red rice, cranberry, bilberry or the like can be used. Also, only one ingredient can be used, or two or more ingredients can also be used together. Furthermore, red ginger is especially favorable to be used. As described above, red ginger comprises another active substance of gingerol for the anti-inflammatory agent. Therefore, both anthocyanidin and gingerol can be easily obtained from red ginger.

Although the content ratio of anthocyanidin to gingerol is not particularly limited, weight ratio (anthocyanidin:gingerol) is 1:100 to 100:1, or preferably 1:10 to 10:1. Or more preferably it is 1:1 to 1:3. If the ratio is less than 1:100 or over 100:1, the anti-inflammatory agent will not function well.

Also, the anti-inflammatory agent or the like in this invention preferably contains shogaol. Chemical formula (2) shows shogaol.

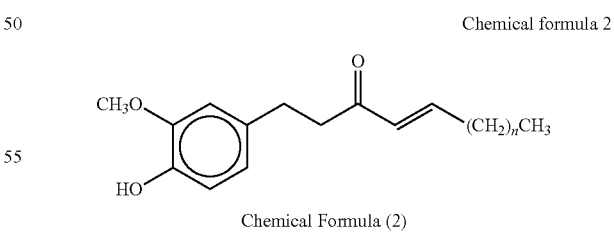

Chemical Formula (2)

From among the above shogaols, 6-shogaol, 8-shogaol and 10-shogaol are preferably contained. Here in the above chemical formula 2, n should be 4 (n=4), 6 (n=6) and 8 (n=8) relatively for the 6-shogaol, 8-shogaol and 10-shogaol.

Also, it is especially preferable that at least 6-shogaol be contained in the inventive anti-inflammatory agent. Furthermore, only one shogaol can be used, or two or more shogaols can be used together.

When red ginger is used as the ingredient for the inventive anti-inflammatory agent or the like, the red ginger extract obtained by the following method can be used as the anti-inflammatory agent or the like.

The above red ginger is preferably defatted. Active substances, like a more appropriate amount of gingerol and an abundance of anthocyanidin or the like can be extracted by using defatted red ginger. Also, the anti-inflammatory agent, or the like, containing more of the substance of shogaols or the like can be obtained.

As for the defatting method, for example, the fat of the red ginger can be removed only by compressing the red ginger. However, the remaining oil of the compressed red ginger can be extracted even more and separated in the defatting solvent (lipophilic organic solvent).

A favorable defatting solvent includes n-hexane, acetone, or the like. Among them, n-hexane is preferably used since the extracted oil can be used for cooking oil and the extract obtained from the defatted red ginger can easily be used for food ingredients. As for the above extracting solvent, one solvent only can be used, or two or more solvents can be used together.

Water, methanol, ethanol, isopropylalcohol, 1,3-butylenglycol, ethylenglycol, propylenglycol, glycerin, ethyl acetate, or the like can be used as a polar solvent for extracting the active substance from the defatted red ginger. One polar solvent only can be used, or two or more polar solvents can be used together.

Water or ethanol can preferably be used as the extracting solvent so that the active substance can efficiently be extracted. Especially, hydrated ethanol does not easily lower the activity of the active substance when extracting, and it is preferably safe to be used for food. Water for extraction includes, but is not limited to, tap water, distilled water, mineral water, ionized alkaline water, deep water or the like.

The temperature for extracting the active substance from the defatted red ginger, when using the hydrate ethanol, is 20 to 100° C., preferably from 60 to 80° C. If the extraction temperature is too low, the active substance will not easily be extracted. On the other hand, if the temperature is too high, the activity of the active substance is lowered.

The concentration of ethanol of the hydrate ethanol as it is being used as the extracting solvent, is 20 to 90 weight percent (wt %), or more preferably 30 to 70 weight percent. If the concentration of ethanol is less than 20 wt %, the active substance may not sufficiently be extracted. And if the ethanol concentration is more than 90 (wt %), the remaining oil of the red ginger may be transferred to the hydrated ethanol. In order to improve the content ratio of the active substance in the hydrated ethanol extraction, it is preferable to repeat the extraction by changing the ethanol concentration in stages.

The extraction of the active substance includes a continuous extraction, a soaking extraction, a countercurrent extraction, a supercritical extraction or the like, which can optionally be used with optional equipment at room temperature or by heating under reflux.

As a specific extraction method, put the extraction ingredient (defatted red ginger) into the tank with the extracting solvent and stir it so that the active substance seeps into the solvent. For instance, when using the hydrated ethanol as the extracting solvent, the extraction is conducted with the extracting solvent approx. 5 to 100 times as much weight as the extraction ingredient for 30 minutes to 2 hours. After the active substance seeps into the solvent, filter it and remove the residue to obtain the extracted liquid. After that, according to the ordinary method, apply the dilution, concentration, drying, refining method or the like to the extracted liquid, so that the inventive anti-inflammatory agent or the like can be obtained.

Also, the refining method includes, for example, an activated carbon treatment, a resin absorption treatment, ion-exchange resin, liquid-liquid countercurrent distribution or the like. However, the refining method can be omitted for the use with food or the like since a large quantity of extract will not be used for food or the like.

The above red ginger extract is characterized by comprising anthocyanin and gingerol.

The anthocyanin content should be 0.5 to 5.0 wt %, preferably 0.5 to 3.5 wt %, more preferably 0.7 to 3.0 wt % or 1.0 to 2.7 wt %, most preferably 1.1 to 2.0 wt %.

Also, the gingerol content should be 1.0 to 10.0 wt %, preferably 1.0 to 7.5 wt %, more preferably 2.0 to 6.5 wt % or most preferably 2.5 to 6.0 wt %.

Also, the above anti-inflammatory agent should preferably contain shogaol as well. Using the shogaol provides the anti-inflammatory agent or the like with a more excellent anti-inflammatory function or the like.

At this time, the shogaol content should be 0.05 to 0.5 wt %, preferably 0.1 to 0.3 wt %, but it is not limited.

The anti-inflammatory agent or the like in this invention preferably contains amino sugar, and/or salt of amino sugar so as to have a more excellent anti-inflammatory function.

The above amino sugar, for example, includes glucosamine, galactosamine, neuraminic acid, N-acetylglucosamine, N-acetylgalactosamine or the like. Among them, glucosamine is preferable. The salt of amino sugar, for example, includes hydrochloride salt, hydrosulfate, phosphoric salt or the like. One kind of salt from among them can be used, or two or more kinds can also used at the same time. Also, either the above amino sugar or the above salt of amino sugar can be used, or both of them can be used together.

In this invention, it is possible to use glucosamine produced from chitin which is obtained by deproteinizing and decalcifying crustacean shell and then by hydrolyzing with concentrated hydrochloric acid, deacetylasing, decoloring, filtering, concentrating, separating, cleansing, and drying. It is also possible to use the commercially-produced glucosamine (e.g. Glucosamine KHF or the like produced by Kyowa Hi Foods Co., Ltd.)

Salt of the glucosamine, for example, includes hydrochloride salt, hydrosulfate (e.g. glucosamine 6-sulfuric acid), phosphate (e.g. glucosamine6-phosphoric acid) or the like. From among them, one only can be used, or two or more can be used together.

Although the relative proportions of the red ginger extract to the amino sugar and/or the salt of amino sugar is not particularly limited, the weight ratio (red ginger extract: amino sugar and/or the salt of amino sugar) is 1:100 to 100:1, preferably 1:50 to 50:1, more preferably 1:5 to 1:20. The anti-inflammatory agent will function well within the above relative proportions.

The active compound like glycosaminoglycan and/or the salt of glycosaminoglycan can also be contained in the anti-inflammatory agent or the like in this invention. Glycosaminoglycan, for example, includes hyaluronic acid, chondroitin, chondroitin sulfate, keratin sulfate, heparin, heparin sulfate, dermatan sulfate or the like.

Chondroitin, chondroitin sulfate or the like is preferably used. From among them, one only can be used, or two or more can be used together. The salt of glycosaminoglycan includes sodium salt, potassium salt, calcium salt or the like. From among them, one only can be used, or two or more can be used together. Either glycosaminoglycan or the salt of the glycosaminoglycan can be used. And the mixture of the above amino sugar and the salt of the amino sugar can be used.

Chondroitin sulfate is a type of mucopolysaccharide which is generally found in animal connective tissues, mainly in cartilage, and is combined with protein to present as proteoglycan in the tissue.

It is possible to use purified chondroitin sulfate or another formula like proteoglycan, cartilage extract or dried cartilage powder.

To obtain the chondroitin sulfate in the form of proteoglycan, firstly process the ingredients, e.g. the cartilage of aquatic animals like sharks, whales or the like, mammals like cows, pigs or the like, or birds by using the conventional method such as the neutral salt method, the oxygen method, the autoclaving method or the like and the extraction method as disclosed in the patent application No. JP2001-247602 or the like. Secondly, remove the fat and solid contents or the like and then dry them. Or, to obtain purified chondroitin or the salt of chondroitin, after removing the fat and solid contents, firstly deproteinize with proteolytic enzyme, then distill it by using the conventional method like the alcohol precipitation method, or according to the purification method as described in e.g. the patent application No. JP2001-247602. Furthermore, it is possible to use chondroitin sulfate or the salt of chondroitin which is commercially available (e.g. chondroitin sulfate sodium salt or the like produced by MARUHA CORPORATION).

The salt of chondroitin sulfate sodium salt includes sodium salt, potassium salt, calcium salt. Among them, sodium salt is preferably used. One kind of salt only can be used, or two or more kinds of salts can be used together.

The preventive or therapeutic agent in this invention can also contain other preventive or therapeutic agents for maladies as needed. Other substances that are effective to prevent or treat arthritis can arbitrarily be added.

Other substances which are effective to prevent or treat arthritis, for example, includes boron, calcium, chromium, copper, magnesium, manganese, selenium, silicon, zinc, S-adenosylmethionine, collagen, collagen hydrolysate, gelatin, gelatin hydrolysate, bromelain, trypsin, chymotripsin, papain, rutin, carotenoid, flavonoid, antioxidant vitamin, γ-linolenic acid, eicosapentaenoic acid, boswellia, capsaicin, cat's claw (uncaria tomentosa), devil's claw (harpagophytum procumbens), feverfew (tanacetum parthenium), nettles (ultica dioica), naiaciamide, turmeric, curcumin or the like. As for the above substances that are effective to prevent or treat arthritis, the purified substances themselves, or a compound containing the above substances, or an extract containing the above substances can be used.

The anti-inflammatory agent or the like in this invention comprises a cyclooxygenase (COX) inhibitory activity.

Cyclooxygenase (COX) is an enzyme which catalyzes two different reactions: one is to synthesize a prostaglandin G2 (PGG2) from an arachidonic acid with two oxygen molecules introduced and added. The other is to form a prostaglandin H2 (PHH2) by separating a 15-hydroperoxide from the PGG2. The COX is also one of the rate-controlling enzymes for prostaglandins (PGs) and thromboxane biosynthesis.

It is known that there are two types of COX, COX-1 and COX-2. COX-1 is a constitutive enzyme and is constitutively expressed in most cellular structures. COX-2 is inductively expressed against the stimulation of cytokine, involved in inflammation, which is interleukin (IL)-1α, the tumor necrosis factor (TNF)-α, lipopoly-saccharides (LPS), the growth factor, or many carcinogenic substances. Inflammation can be controlled by inhibiting the COX-2. Therefore, COX-2 has a soothing effect against articular inflammation, an analgesic effect, an antipyretic effect, or the like.

The anti-inflammatory agent or the like in this invention promotes the activity of COX-1 and inhibits COX-2 as well. The anti-inflammatory agent or the like in this invention can selectively inhibit only COX-2 so that it reduces the side effects such as gastrointestinal damage, kidney damage or the like, and shows an excellent anti-inflammatory effect, an analgesic effect and an antipyretic effect.

Also, the anti-inflammatory agent or the like in this invention has preventive and therapeutic effects on adjuvant arthritis, collagen arthritis, or the like. Thus, a chronic inflammation such as rheumatism or the like can be controlled, and such diseases can be effectively prevented and treated.

Furthermore, the anti-inflammatory agent or the like in this invention can effectively prevent and treat even acute inflammation.

This invention can be applied without limitation to chlamydial arthritis, chronic absorptive arthritis, enteropathy-related arthritis, gonococcal arthritis, gouty arthritis, Jaccoud's arthritis, juvenile arthritis, lyme arthritis, alcaptonuric arthritis, purulent arthritis, degenerative arthritis, periarthritis humeroscapularis, arthritis which caused by excessive exercise, chronic rheumatoid arthritis, or the like. This invention is especially effective against chronic rheumatoid arthritis.

The anti-inflammatory agent or the like in this invention can be used as an ingredient for any food and drink such as, confectionary (chewing gums, candies, caramels, chocolates, cookies, jellies, gummies, tablet shaped sweets or the like), noodles (Japanese buckwheat noodles called Soba, Japanese wheat noodles called Udon, Chinese noodles called Ramen or the like), dairy food (milk, ice cream, yogurt, or the like), seasoning (fermented bean paste called Miso, Soy sauce called Shoyu, or the like), soups, drinks (juice, coffee, black tea, green tea, carbonated drink, or the like) including general foods and healthy food (tablet type, capsule type or the like), nutritional supplements (nutritious supplement drink or the like). The anti-inflammatory agent or the like in this invention can be used for the above foods and drinks.

According to the type of the above foods and drinks, the following ingredients can be added:

Glucose, fructose, sucrose, maltose, sorbitol, stevioside, corn syrup, lactose, citric acid, tartaric acid, malic acid, saccinic acid, lactic acid, L-ascorbic acid, dl-α-tocopherol, sodium erythorbate, glycerin, propylene glycol, glycerin fatty acid ester, polyglycerol fatty acid ester, sucrose fatty acid ester, sorbitan fatty acid ester, propylene glycol fatty acid ester, Arabian gum, carrageenan, casein, gelatin, pectine, agar-agar (gelatin made from seaweed), vitamin B family, nicotinic-acid amide, pantothenate acid calcium, amino acids, calcium salts, pigment, aroma chemicals, preservatives, or the like.

Also, other antioxidants or compounding ingredients of healthy food include the antioxidant reduced ascorbic acid or vitamin C and also the antioxidants, vitamin E, reduced glutacin, tocotrienol, vitamin A derivative, lycopene, rutin, astaxanthin, zeaxanthin, fucoxanthin, uric acid, ubiquinone, coenzyme Q-10, folic acid, garlic extract, allicin, sesamin, lignan, catechin, isoflavone, chalcone, tannins, flavonoids, coumarin, isocoumarines, blueberry extract), ingredients for healthy food (V. (vitamin) A, V.B1, V.B2, V.B6, V.B12, V.C, V.D, V.E, V.P, choline, niacin, pantothenic acid, calcium folic acid, EPA, oligosaccharide, dietary fiber, squalene, soybean lecithin, taurine, dunalliela, protein, octacosanol, DHA, egg-yolk lecithin, linoleic acid, lactoferrin, magnesium, zinc, chrome, selenium, kalium, hem iron, oyster extract, chitosan, chitin oligosaccharides, turmeric, licorice, corbiculidae extract, snapping turtle, sweetroot, lycii fructus, cinnamomi cortex, crataegus cuneata, ganoderma, plantain, chamomilla, chamomile, dandelion, hibiscus, honey, pollen, royal jelly, lime, lavender, rose hip, rosemary, sage, bifidobacteria, *streptococcus faecalis, lactobacillus*, wheat germ oil, sesame oil, perilla oil, soybean oil, medium chain fatty acid, agaricus, ginko biloba extract, brown rice germ oil, leechee, onion, DHA, EPA, DPA, *rubus suavissimus* s. *lee*, plant worm (cordyceps sineusis saccardo), garlic, larvae of a bee, papaya, pu-erh-tea, propolis, Acer nikoense, hericium erinaceum, royal jelly, saw palmetto, hyaluronic acid, gaba, harp seal oil, shark cartilage, lecithin, phosphatydyl serine, panax notoginseng, mulberry leaf, soybean extract, echinacea purpurea, acanthopanax senticosus, barley extract, olive leaf, olive, gymnema, banaba, salacia reticulata, garcinia, chitosan, saint john's wort, jujube, carrot, passion flower, broccoli, placenta, coix lacryma-bobi, grape seed, peanut skin, black cohosh, milk thistle, laurel, sage, rosemary, apocynum venetum, black vinegar, bitter gourd, maca, carthamus tinctorius, linseed, oolong tea, flower aculeus, *pyracantha fortuneana*, hippophoe rhomnoidesl, caffeine, capsaicin, xylo-oligosaccharide, buckwheat, citrus, dietary fiber, protein, prune, spirulina, young green barley leaf, nucleic acid, natural yeast, shiitake mushroom (*lentinus edodes*), Japanese plum, extract of deep sea shark, morinda citrifolia, oyster, snapping turtle, champinion, common plantain, acerola, pineapple, banana, peach, apricot, melon, strawberry, raspberry, orange, fucoidan, acer nikoense, cranberry, zinc, iron, ceramide, silk peptide, glycine, niacin, chaste tree berry, L-cysteine, red wine leaf, red wine leaf (*Vitis vinifera*), millet, horsetail, bition, centrlla asiatica, *lonicera caerulea*, pycnogenol, petasites japonicus, rhubarb, clove, rosemary, catechin, pu-erh, citric acid, beer yeast, mellilot, black zinger, curcuma zedoaria, nattokinase, ang-khak (Chinese red rice), tocotrienol, lactoferrin, cinnamon, tartary buckwheat, cocoa, citrus seed extract, perilla fruit extract,α-lipoic acid, green coffee beans. These can be also used as anti-inflammatory agents to maintain good health. From among the above ingredients, one only can be used, or two or more can be used together, A more specific use of the extracting method is herein described. Firstly, spray-dry or freeze-dry the anti-inflammatory agent or the like in this invention with powdered cellulose, then make it a powder, a granule, a tablet, or liquid to easily use with different kinds of food and drinks (ready-to eat meals or the like). Also, it is possible to dissolve the anti-inflammatory agent or the like in this invention into, for instance, oil and fat, ethanol, glycerin, or a mixture of these substances, and to use such a liquid for dry food or drinks. Also it is possible to make it into a powder or granule by mixing it with a binder such as Arabian gum, dextrin, or the like to add to dry food or drinks.

The total amount of the active substance in this inventive anti-inflammatory agent or the like, which is added to the food and drinks, is preferably 1 to 20 wt % or less, since the major objective of this invention is health maintenance.

The inventive anti-inflammatory agent or the like can be used as the raw material of medicines (including drugs and quasi-drugs). The inventive anti-inflammatory agent or the like can be appropriately mixed with raw materials for drug formulations, for instance, vehicles (glucose, sucrose, white soft sugar, sodium chloride, starch, calcium carbonate, kaolin, crystalline cellulose, cacao oil, hydrogenated vegetable oil, talc, or the like), binders (distilled water, normal saline solution, ethanol in water, ethanolic solution, simple syrup, dextrose in water, starch solution, gelatin solution, carboxymethyl cellulose, potassium phosphate, polyvinyl pyrrolidone, or the like), disintegrating agents (alginate sodium, agar-agar, sodium hydrogen carbonate, sodium lauryl sulphate, stearic acid monoglyceride, starch, lactose, powdered aracia, gelatin, ethanol, or the like), suppressive agents for disintegration (white soft sugar, stearin, cacao oil, hydrogenated oil, or the like), absorption promoters (quaternary ammonium base, sodium lauryl sulphate, or the like), adsorbents (glycerin, starch, lactose, kaolin, bentonite, silic acid, or the like), lubricant agents (purified talc, stearate, polyethyleneglycol, or the like)

The inventive anti-inflammatory agent or the like can be orally administered in the form of tablets, pills, soft or hard capsules, subtle granules, powders, granules, liquids, or the like. However, it can also be parenterally administered in the different forms of solution or together with a dispersant, a suspending agent, a stabilizer, or the like such as a medical skin patch, a lotion, an ointment, a cream or the like.

The applied dose can be adjusted according to the method of administration, the condition of the disease, the age of the patient, or the like. However, adults can normally take approx. 0.5 to 5,000 mg of an active substance per day, while children can take 0.5 to 3,000 mg per day.

The compounding ratio of the inventive anti-inflammatory agent or the like can be adjusted according to the mode of administration. When the dietetic composition is orally administered or mucosally administered, the applied dose is preferably 0.3 to 15.0 wt %. When the dietetic composition is parenterally administered, the dose is preferably 0.01 to 10 wt %. The dose varies depending on the conditions. Therefore, a dose which is less than the above-stated amount may be sufficient, or a greater amount may sometimes be needed.

The anti-inflammatory effect can be reasonably expected by using the inventive anti-inflammatory agent or the like for a drug for external skin use (including cosmetics, drugs, and quasi-drugs).

The inventive anti-inflammatory agent or the like can be mixed with cosmetics such as emulsions, soaps, facial cleansers, bath agents, creams, skin lotions, colognes, shaving creams, shaving lotion, beauty oils, tanning lotions, sunscreen lotions, face powders, foundations, perfumes, facial masks, nail creams, nail enamels, nail-polish removers, eyebrow pencils, blushers, eye creams, eye shadows, mascaras, eye liners, Lip sticks, lip creams, shampoos, hair conditioners, hairdyes, dispersion liquids, cleansing preparations, or the like.

Also, the inventive anti-inflammatory agent or the like can be mixed with drugs and quasi-drugs such as ointments, cream pharmaceuticals, liquids for external use or the like.

Within the functional range of the inventive anti-inflammatory agent or the like, the above items for external skin use can be also mixed with the ingredients of cosmetics, quasi-drugs, or the like. Those ingredients include, for example, oil, higher alcohol, fatty acids, ultraviolet absorbers, powders, pigments, surface active agents, polyhydric alcohol and sugar, polymers, biologically active ingredients, solvents, antioxidants, aroma chemicals (perfume material), antiseptics. However, those ingredients usable in the present invention are not limited to these examples.

(1) Specific Examples of Oil

Ester-type oil phase ingredient: Triglyceryl 2-ethylhexanoate, cetyl 2-ethylhexanoate, isopropyl myristate, butyl myristate, isopropyl palmitate, ethyl stearate, octyl palmitate, isocetyl isostearate, butyl stearate, butyl myristate, ethyl linoleate, isopropyl linoleate, ethyl oleate, isocetyl myristate, isostearyl myristate, isostearyl palmitate, octyldodecyl myristate, isocetyl isostearate, diethyl sebacate, diisopropyl adipate, isoarachyl neopentanoate, caprylic-capric acid triglyceride, trimethylolpropane tri-2-ethylhexanoate, trimethylolpropane triisostearate, pentaerythritol tetra-2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl myristate, isostearyl myristate, isocetyl palmitate, isostearyl palmitate, octyl stearate, isocetyl stearate, isodecyl oleate, octyldodecyl oleate, octyldodecyl linoleate, isopropyl isostearate, cetostearyl 2-ethylhexanoate, stearyl 2-ethylhexanoate, hexyl isostearate, ethylene glycol dioctanoate, ethylene glycol dioleate, propylene glycol dicaprate, propylene glycol di(caprylate/caprate), propylene glycol dicaprylate, neopentyl glycol dicaprate, neopentyl glycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isocetyl isostearate, isostearyl isostearate, octyldecyl isostearate, polyglycerin oleate, polyglycerin isostearate, dipropyl carbonate, dialkyl carbonate (C12-18), triisocetyl citrate, triisoarachyl citrate, triisooctyl citrate, lauryl lactate, myristyl lactate, cetyl lactate, octyldecyl lactate, triethyl citrate, acetyltriethyl citrate, acet-yltributyl citrate,-trioctyl citrate, diisostearyl malate, 2-ethylhexyl hydroxystearate, 2-ethylhexyl succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoylhydroxystearate, stearyl 12-stearoylhydroxystearate and isostearyl 12-stearoylhydroxystearate. From among the above ingredients, one only can be used, or two or more can be used together.

(Hydrocarbon-type oil phase ingredient) Squalane, liquid paraffin, a-olefin oligomer, isoparaffin, ceresin, paraffin, liquid isoparaffin, polybutene, microcrystalline wax and vaseline.

(Animal and plant oil, hardened oil thereof, and wax of natural origin) Animal oils and hardened oils thereof, such as beef tallow, hardened beef tallow, lard, hardened lard, horse oil, hardened horse oil, mink oil, orange roughy oil, fish oil, hardened fish oil and egg yolk oil; plant oils and hardened oils thereof such as avocado oil, almond oil, olive oil, cacao oil, apricot kernel oil, kukui nut oil, sesame oil, wheat germ oil, rice germ oil, rice bran oil, safflower oil, shea butter, soybean oil, evening primrose oil, perilla oil, tea seed oil, tsubaki oil (camellia japonica oil), corn oil, rapeseed oil, hardened rapeseed oil, palm kernel oil, hardened palm kernel oil, palm oil, hardened palm oil, peanut oil, hardened peanut oil, castor oil, hydrogenated castor oil, sunflower oil, grape seed oil, jojoba oil, hardened jojoba oil, macadamia nut oil, meadowfoam seed oil, cottonseed oil, hardened cottonseed oil, conoanut oil, hardened cocoanut oil; and waxes such as beeswax, high acid number beeswax, lanolin, reduced lanolin, hardened lanolin, liquid lanolin, carnauba wax and montan wax. From among the above ingredients, one only can be used, or two or more can be used together.

(Silicone-type oil phase ingredient) Dimethylpolysiloxane, methylphenylpolysiloxane, methylcyclopolysiloxane, octamethylpolysiloxane, decamethylpolysiloxane, dodecamethylcyclosiloxane, methylhydrogenpolysiloxane, polyether-modified organopolysiloxane, dimethylsiloxanemethylcetyloxysiloxane copolymer, dimethylsiloxanemethylstearoxysiloxane copolymer, alkyl-modified organopolysiloxane, terminal-modified organopolysiloxane, amino-modified silicone oil, amino-modified organopolysiloxane, dimethiconol, silicone gel, acryl silicone, trimethylsiloxysilicic acid and silicone RTV rubber. From among the above ingredients, one only can be used, or two or more can be used together.

(Fluorine-type oil phase ingredient) Perfluoropolyether, fluorine-modified organopolysiloxane, fluorinated pitch, fluorocarbon, fluoroalcohol and fluoroalkyl-polyoxyalkylene-comodified organopolysiloxane. From among the above ingredients, one only can be used, or two or more can be used together.

(2) Specific Examples of Higher Alcohol

Lauryl alcohol, myristyl alcohol, cetyl alcohol, stearyl alcohol, isostearyl alcohol, oleyl alcohol, behenyl alcohol, 2-ethylhexanol, hexadecyl alcohol and octyl dodecanol. From among the above ingredients, one only can be used, or two or more can be used together.

(3) Specific Examples of Fatty Acid

Caprylic acid, capric acid, undecylenic acid, lauric acid, myristic acid, palmitic acid, palmitoleic acid, stearic acid, isostearic acid, oleic acid, linoleic acid, linolenic acid, arachic acid, arachidonic acid, behenic acid, erucic acid and 2-ethylhexanoic acid. From among the above ingredients, one only can be used, or two or more can be used together.

(4) Specific Examples of Ultraviolet Absorber

Para-aminobenzoic acid, amyl para-aminobenzoate, ethyldihydroxypropyl para-aminobenzoate, glyceryl para-aminobenzoate, ethyl para-aminobenzoate, octyl para-aminobenzoate, octyldimethyl para-aminobenzoate, ethylene glycol salicylate, octyl salicylate, triethanolamine salicylate, phenyl salicylate, butylphenyl salicylate, benzyl salicylate, homomenthyl salicylate, benzyl cinnamate, octyl para-methoxycinnamate, 2-ethylhexyl para-methoxycinnamate, glyceryl mono-2-ethyl hexanoate di-para-methoxycinnamate, isopropyl para-methoxycinnamate, diethanolamine para-methoxyhydrocinnamate, diisopropyl diisopropylcinnamic acid ester mixture, urocanic acid, ethyl urocanate, hydroxymethoxybenzophenone, hydroxymethoxybenzophenone sulfonic acid and a salt thereof, dihydroxymethoxybenzophenone, sodium dihydroxymethoxybenzophenonedisulfonate, dihydroxybenzophenone, dihydroxydimethoxybenzophenone, hydroxyoctoxybenzophenone, tetrahydroxybenzophenone, butylmethoxydibenzoylmethane, 2,4,6-trianilino-p-(carbo-2-ethylhexyl-1-oxy)-1,3,5-triazine, 2-(2-hydroxy-5-methylphenyl) benzotriazole, methyl-0-aminobenzoate, 2-ethylhexyl-2-cyano-3,3-diphenylacrylate, phenylbenzimidazole sulfuric acid, 3-(4-methylbenzylidene)camphor, isopropyldibenzoylmethane, 4-(3,4-dimethoxyphenylmethylene)-2,5-doxy-1-imidazolidinepropionate, and polymer derivatives and silane derivatives thereof. From among the above ingredients, one only can be used, or two or more can be used together.

(5) Specific Examples of Powder and Pigment

Pigments such as Food Red 104, Food Red 201, Food Yellow 4, Food Blue 1 and Food Black 401; lake pigments such as Food Yellow 4 AL lake and Food Yellow 203 BA lake; polymers such as nylon powder, silk powder, urethane powder, Teflon® powder, silicone powder, polymethyl methacrylate powder, cellulose powder, starch, silicone elastomer spherical powder and polyethylene powder; color pigments such as yellow iron oxide, red iron oxide, black iron oxide, chromium oxide, carbon black, ultramarine and iron blue; white pigments such as zinc oxide, titanium oxide and cerium oxide; extender pigments such as talc, mica, sericite, kaolin and plate barium sulfate; pearl pigments such as mica titanium; metal salts such as barium sulfate, calcium carbonate, magnesium carbonate, aluminum silicate and magnesium silicate; inorganic powders such as silica and alumina; metal soaps such as aluminum stearate, magnesium stearate, zinc palmitate, zinc myristate, magnesium myristate, zinc laurate and zinc undecylenate; bentonite; smectite; and boron nitride. From among the above ingredients, one only can be used, or two or more can be used together.

The shape (e.g., sphere, bar, needle, plate, amorphous, scale, spindle) and the particle size of these powders are not particularly limited. These powders may or may not be previously surface-treated by a conventionally known surface treatment such as fluorine compound treatment, silicone treatment, silicone resin treatment, pendant treatment, saline coupling agent treatment, titanium coupling agent treatment, lubricant treatment, N-acylated lysine treatment, polyacrylic acid treatment, metal soap treatment, amino acid treatment, lecithin treatment, inorganic compound treatment, plasma treatment and mechanochemical treatment. From among the above ingredients, one only can be used, or two or more can be used together.

(6) Specific Examples of Surfactant

Anionic surfactant: Fatty acid soap, a-acyl sulfonate, alkyl sulfonate, alkylallyl sulfonate, alkylnaphthalene sulfonate, alkyl sulfate, POE alkyl ether sulfate, alkylamide sulfate, alkyl phosphate, POE alkyl phosphate, alkylamide phosphate, alkyloylalkyl taurine salt, N-acylamino acid salt, POE alkyl ether carbonate, alkyl sulfosuccinate, sodium alkylsulfoacetate, acylated hydrolyzed collagen peptide salt and perfluoroalkylphosphoric acid ester. From among the above ingredients, one only can be used, or two or more can be used together.

Cationic surfactant: Alkyltrimethylammonium chloride, stearyltrimethylammonium chloride, stearyltrimethylammonium bromide, cetostearyltrimethylammonium chloride, distearyldimethylammonium chloride, stearyldimethylbenzylammonium chloride, behenyltrimethylammonium bromide, benzalkonium chloride, behenic acid amidopropyldimethyl hydroxypropylammonium chloride, diethylaminoethylamide stearate, dimethylaminoethylamide stearate, dimethylaminopropylamide stearate and lanolin derivative quaternary ammonium salt. From among the above ingredients, one only can be used, or two or more can be used together.

(Amphoteric surfactant) Carboxybetaine type, amidobetaine type, sulfobetaine type, hydroxysulfobetaine type, amidosulfobetaine type, phosphobetaine type, aminocarboxylate type, imidazoline derivative type and amidoamine type. From among the above ingredients, one only can be used, or two or more can be used together.

(Nonionic surfactant) Propylene glycol fatty acid ester, glycerin fatty acid ester, polyglycerin fatty acid ester, sorbitan fatty acid ester, POE sorbitan fatty acid ester, POE sorbitol fatty acid ester, POE glycerin fatty acid ester, POE alkyl ether, POE fatty acid ester, POE hydrogenated castor oil, POE castor oil, POE-POP copolymer, POE-POP alkyl ether, polyether-modified silicone lauric acid alkanolamide, alkylamine oxide and hydrogenated soybean phospholipid. From among the above ingredients, one only can be used, or two or more can be used together.

(Natural-type surfactant) Lecithin, saponin and sugar-type surfactant. One ingredient only can be used, or two or more can be used together.

(7) Specific Examples of Polyhydric Alcohol and Sugar

Ethylene glycol, diethylene glycol, polyethylene glycol, propylene glycol, dipropylene glycol, polypropylene glycol, glycerin, diglycerin, polyglycerin, 3-methyl-1,3-butanediol, 1,3-butylene glycol, sorbitol, mannitol, raffinose, erythritol, glucose, sucrose, fruit sugar, xylitol, lactose, maltose, maltitol, trehalose, alkylated trehalose, mixed isomerized sugar, sulfated trehalose and pullulan. Chemically modified products thereof can also be used. From among the above ingredients, one only can be used, or two or more can be used together.

(8) Specific Examples of Polymer Compound

Anionic polymer compounds such as acrylic acid ester/methacrylic acid ester copolymer (PLUS-SIZE, produced by Sogokagaku K.K.), vinyl acetate/crotonic acid copolymer (Resin 28-1310, produced by NSC), vinyl acetate/crotonic acid/vinyl neodecanate copolymer (28-2930, produced by NSC), methyl vinyl ether maleic acid half ester (GANTREZ ES, produced by ISP), T-butyl acrylate/ethyl acrylate/methacrylic acid copolymer (RUBIMER, produced by BASF), vinylpyrrolidone/vinyl acetate/vinyl propionate copolymer (RUBISCOL VAP, produced by BASF), vinyl acetate/crotonic acid copolymer (RUBISET CA, produced by BASF), vinyl acetate/crotonic acid/vinylpyrrolidone copolymer (RUBISET CAP, produced by BASF), vinylpyrrolidone/acrylate copolymer (RUBIFLEX, produced by BASF), acrylate/acrylamide copolymer (ULTRAHOLD, produced by BASF), vinyl acetate/butyl maleate-isobornyl acrylate copolymer (ADVANTAGE, produced by ISP), carboxy vinyl polymer (CARBOPOL, produced by BF Goodrich) and acrylic acid-alkyl methacrylate copolymer (PAMUREN, produced by BF Goodrich); amphoteric polymer compounds such as acetic acid amphoteric compound of dialkylaminoethyl methacrylate polymer (YUKAFORMER, produced by Mitsubishi Chemical) and octylacrylamide acrylate/hydroxypropyl acrylate/butylaminoethyl methacrylate copolymer (AMPHOMER, produced by NSC); cationic polymer compounds such as quaternized compound of vinylpyrrolidone/dimethylaminoethyl methacrylate (GAFQUAT, produced by ISP) and methyl vinyl imidazolium chloride/vinylpyrrolidone copolymer (RUBICOTE, produced by BASF); and nonionic polymer compounds such as polyvinylpyrrolidone/vinyl acetate copolymer (RUBISCOL VA, produced by BASF) and vinylpyrrolidone/dimethylaminoethyl methacrylate copolymer (COPOLYMER VC713, produced by ISP).

In addition, polymer compounds of natural origin, such as cellulose and derivatives thereof, calcium alginate, pullulan, agar, gelatin, tamarind seed polysaccharides, xanthane gum, carrageenan, high-methoxyl pectin, low-methoxyl pectin, guar gum, gum arabi, crystal cellulose, arabino galactan, karaya gum, tragacanth gum, alginic acid, albumin, casein, cardrun, gellan gum and dextran, can also be suitably used. From among the above ingredients, one only can be used, or two or more can be used together.

(9) Specific Examples of Biologically Active Ingredient

The biologically active ingredient may include substances which are capable of imparting some biological activity to skin, when such a substance is applied to the skin. Specific examples thereof may include: whitening ingredient, age resistor, ultraviolet protection, slimming agent, skin tightening agent, antioxidant, hair restorer, hair growing agent, moisturizer, blood circulation accelerator, antibacterial agent, bactericide, desiccant, cooling agent, warming agent, vitamin compound, amino acid, wound healing accelerator, torpent, analgetic, cell activator and enzyme ingredient.

Suitable examples of the ingredient to be blended therefor may include: angelica extract, avocado extract, hydrangea extract, althea extract, arnica extract, aloe extract, apricot extract, apricot core extract, ginkgo extract, fennel extract, turmeric extract, oolong tea extract, rose fruit extract, echinacea leaf extract, scutellaria root extract, phellodendron bark extract, goldthread extract, barley extract, hypericum extract, white nettle extract, watercress extract, orange extract, sea salt, seaweed extract, hydrolyzed elastin, hydrolyzed wheat powder, hydrolyzed silk, chamomile extract, carrot extract, artemisia capillaris extract, glycyrrhiza extract, sabdariffa extract, *pyracantha fortuneana* fruit extract, cinchona extract, cucumber extract, guanosine, gardenia extract, sasa albo-marginata extract, sophora root extract, walnut extract, grapefruit extract, clematis extract, chlorella extract, mulberry bark extract, gentian extract, black tea extract, yeast extract, burdock extract, fermented rice bran extract, rice germ oil, comfrey extract, collagen, cowberry extract, asiasarum root extract, bupleurum falcatum root extract, umbilical cord extract, salvia extract, saponaria extract, bamboo grass extract, crataegus extract, zanthoxylum fruit extract, shiitake mushroom extract, rehmannia root extract, lithospermum root extract, perilla extract, linden extract, filipendula extract, peony root extract, calamus rhizome extract, birch extract, horsetail extract, ivy extract, hawthorn extract, sambucus nigra extract, yarrow extract, peppermint extract, sage extract, mallow extract, cnidium rhizome extract, swertia herb extract, soy extract, jujube extract, wild thyme extract, green tea extract, clove extract, cogon extract, citrus unshiu peel extract, angelica root extract, calendula extract, peach seed extract, bitter orange extract, houttuynia extract, tomato extract, natto extract, ginseng extract, garlic extract, wild rose extract, hibiscus sabdariffa flower extract, ophiopogon tuber extract, parsley extract, honey, witch hazel extract, pellitory extract, isodonis extract, matricaria extract, loquat extract, coltsfoot extract, butterbur scape extract, Poria cocos extract, butcher bloom extract, grape extract, propolis, luffa extract, safflower extract, peppermint extract, linden extract, peony extract, hop extract, pine extract, horse chestnut extract, skunk cabbage extract, sapindaceae extract, balm mint extract, peach extract, cornflower extract, eucalyptus extract, saxifrage extract, coix seed extract, mugwort extract, lavender extract, apple extract, lettuce extract, lemon extract, Chinese milk vetch extract, rose extract, rosemary extract, Roman chamomile extract and royal jelly extract.

Other examples may include biopolymers such as deoxyribonucleic acid, mucopolysaccharide, sodium hyaluronate, sodium, elastin, chitin, chitosan and hydrolyzed eggshell membrane; moisture retentive ingredients such as amino acid, hydrolyzed peptide, sodium lactate, urea, sodium pyrrolidonecarboxylate, betaine, whey and trimethylglycine; oily ingredients such as sphingolipid, ceramide, phytosphingosine, cholesterol, cholesterol derivatives and phospholipid; anti-inflammatory such as E-aminocaproic acid, glycyrrhizic acid, glycyrrhetic acid, lysozyme chloride, guaiazlene and hydrocortisone; vitamins such as vitamin A, vitamin B2, vitamin B6, vitamin D, vitamin E, calcium pantothenate, biotin and nicotinic acid amide; active ingredients such as allantoin, diisopropylamine dichloroacetate and 4-aminomethylcyclohexanecarboxylic acid; antioxidants such as tocopherol, carotenoid, flavonoid, tannin, lignin and saponin; cell activators such as a-hydroxy acid and hydroxy acid; blood circulation accelerators such as y-orizanol and vitamin E derivatives; wound healing agents such as retinol and retinol derivatives; whitening agents such as albumin, kojic acid, placenta extract, sulfur, ellagic acid, linoleic acid, tranexamic acid and glutathione; and hair growing agents such as cepharanthine, glycyrrhiza extract, capsicum tincture, hinokitiol, iodized garlic extract, pyridoxine hydrochloride, DL-a-tocopherol, DL-a-tocopheryl acetate, nicotinic acid, nicotinic acid derivatives, calcium pantothenate, D-pantothenyl alcohol, acetyl pantothenylethyl ether, biotin, allantoin, isopropylmethylphenol, estradiol, ethynyl estradiol, capronium chloride, benzalkonium chloride, diphenhydramine hydrochloride, Takanal, camphor, salicylic acid, vanillylamide nonylate, vanillylamide nonanoate, pyroctone olamine, glyceryl pentadecanoate, L-menthol, mononitroguaiacol, resorcinol, y-aminobutyric acid, benzethonium chloride, mexiletine hydrochloride, auxin, female hormone, cantharis tincture, cyclosporine, zinc pyrithione, hydrocortisone, minoxidil, polyoxyethylene sorbitan monostearate, peppermint oil and SADANISHIKI extract. From among the above ingredients, one only can be used, or two or more can be used together.

(10) Specific examples of antioxidant Sodium hydrogensulfite, sodium sulfite, erythorbic acid, sodium erythorbate, dilauryl thiodipropionate, tocopherol, tolylbiguanide, nordihydroguaiaretic acid, parahydroxy anisole, butylhydroxy anisole, dibutylhydroxy toluene, ascorbyl stearate, ascorbyl palmitate, octyl gallate, propyl gallate, carotenoid, flavonoid, tannin, lignin, saponin and plant extracts having antioxidant effect, such as apple extract and clove extract. From among the above ingredients, one only can be used, or two or more can be used together.

(11) Specific examples of solvent Purified water, ethanol, lower alcohol, ethers, LPG, fluorocarbon, N-methylpyrrolidone, fluoroalcohol, volatile linear silicone and next generation freon (such as fluorocarbon, chlorofluorocarbon, CFC). From among the above ingredients, one only can be used, or two or more can be used together.

EXAMPLE

More specific examples in this invention are herein described.

Example 1

Method for Manufacturing the Anti-Inflammatory Agent or the Like (Red Ginger Extract)

The anti-inflammatory agent or the like (red ginger extract) can be manufactured by the following method.

Indonesia's red ginger is used as an ingredient. Firstly, slice and dry the red ginger, then obtain 100 kilograms of the dried red ginger. Fracture 10 kilograms of the red ginger to make it compressed. Flux the compressed red ginger with four times its weight of n-hexane to remove the remaining oil from the compressed red ginger, and obtain the defatted red ginger. Then, process the defatted red ginger with hydrated ethanol (ethanol concentration: 40 wt %) at a temperature of 80 degrees Celsius (80° C.) for two hours, and dry out the ethanol extract to obtain 1.5 grams of red ginger extract (Example 1). HPLC (High Performance Liquid Chromatography) for analyzing the substances contained in the red ginger extract (Example 1) shows 2.0 wt % of 6-gingerol, 1.0 wt % of anthocyanin, 0.2 wt % of 6-shogaol, and 0.5 wt % of 10-shogaol.

Example 2

Method of Manufacturing each Substance Contained in the Red Ginger Extract

Substances contained in the red ginger, e.g. 6-gingerol (Example 2-1), 4-gingerol (Example 2-2), 8-gingerol (Example 2-3), 10-gingerol (Example 2-4), 6-shogaol (Example 2-5), and 10-shogaol (Example 2-6) as well as anthocyanin fraction (Example 2-7) were obtained by using the following methods.

Example 2-1

Method of Manufacturing 6-Gingerol

Fracture one kilogram of red ginger, and add three times its volume of hexane. Then, stir it at a temperature of 60° C. After that, filter the extract and concentrate the filtrate to obtain 70 grams of the hexane extract. Repeatedly separate and refine the hexane extract by reversed-phase HPLC (Column: Inertsil ODS, 10×250 mm, product of GL Sciences Inc., Mobile phase: 70% methanol, 3.5 mL/min. UV detection: 280 nm) to obtain the 6-gingerol (50 mg). As a result of the comparison with the NMR (1H-13H) spectrum of the commercially available standard 6-gingerol, the substance obtained by this method was identified as 6-gingerol.

Examples 2-2 to 2-4

Methods of Manufacturing Types of Gingerol other than 6-Gingerol, and Methods of Manufacturing Shogaol The extract obtained in Example 1 by HPLC (Prep. ODS, 20×250 mm, 90% methanol) was separated and refined, and 5 mg of 4-gingerol (Example 2-2), 6 mg of 8-gingerol (Example 2-3), 10-gingerol (Example 2-4), 6-shogaol (Example 2-5) and 10-shogaol (Example 2-6) were obtained.

Examples 2-7

Method of Manufacturing Anthocyanin Fraction

Fracture red ginger (1 kg), add five times its volume of methanol containing 1% of formic acid, then stir it at a temperature of 70° C. for two hours. After that, filter the extract and concentrate the filtrate to obtain 100 grams of the extract. Suspend the extract (10 g) in water (100 mL). Then put the suspended extract in the column processed with DIAION HP-20 (200 g). After that, clean the column using water (200 mL). and elute it with 30% ethanol. Concentrate the eluate to obtain the anthocyanin fraction. The anthocyanin content of the anthocyanin fraction was 1%.

Test Example 1

Preventive Effect on Adjuvant Arthritis

To verify the preventive effect of the red ginger extract on the adjuvant arthritis, the following test was conducted.

Firstly, subcutaneously administer the adjuvant to the right tarsus of the rats under the following condition so that the arthritis is caused in the mice. On the second day that the arthritis is induced, orally administer the red ginger extract to the rats for four consecutive weeks by the following method, and regularly observe the tarsus edema of the rats and the anti-inflammatory effect of the test substance.

1. Method of Preparing the Test Substance
1-1: Test Substance
Weigh at once the two-day doses of the red ginger extract as the test substance described in Example 1, and use the red ginger extract suspended with the 0.5% CMC-Na. At this time, prepare the high-dose test substance (10 mg/5 mL/kg). Then, concentrate the liquid to prepare the low-dose test substance (1 mg/5 mL/kg).
1-2: Positive Control Substance (Comparative Example)
Weigh the necessary amount of Indomethacin (Lot No. 122K0718, Sigma-Aldrich, Inc.) which is commercially available. Then prepare freshly the positive control substance with the injection solvent until it becomes 0.5 mg/5 mL/kg. Then, dispose of it after all the administrations have been completed.
1-3: Solvent
In this test, a 0.5% CMC-Na aqueous solution was used as the solvent. To obtain the solvent, first weigh the necessary amount of carboxymethylcellulose-Na (CMC sodium Lot 082K-153, Sigma-Aldrich, Inc.). Then, dissolve it with the commercially-available injection solvent until it reaches a specific concentration. Store it in a hermetic container and place it in a cool, dark place. Use the solvent within seven days after the preparation.
2. Firstly, obtain 28 mice (7-week-old, SD (CrjBgi:CD) IGS mice, male SPF) from ORIENT CO., LTD. Then, quarantine and naturalize the mice for more than 7 days. After observing the mice during the period of naturalization and quarantine, use the mice that are alive and which have no problems in the weight and general status. When the mice were grouped, the weight ranged from 279.3 to 328.7 g. When the inflammation was induced, the weight ranged from 283.7 to 333.9 g. When the autopsy was conducted, the weight ranged from 293.4 g to 440.8 g.
3. Administration
The test substance was forcibly administered to the mice through a stomach sonde or syringe once a day for a period of 28 days after the inflammation was induced.
4. Grouping
As shown in the chart below, there are 4 groups, and each group has seven examples (i.e. 7 mice). The test substance was orally administered to each mouse for 28 days from the day after the inflammation was induced. During the period when the test substance was administered, the edema of the right tarsus of each mouse was X-rayed twice a week. From the day after the test was completed, the right and left tarsuses of each mouse were X-rayed twice a week, and the effect of the test substance on the bone was verified.

CHART 1

| Group | Test substance | Amount (mg/kg) | Dosing times (time/day) | Dosing days (days) | No. of animals | (ID No.) |
|---|---|---|---|---|---|---|
| Group 1(control) | Solvent | 0 | 1 | 28 | 7 | (11-17) |
| Group 2(Low dose) | Red ginger extract | 1 | 1 | 28 | 7 | (21-27) |
| Group 3(High dose) | Red ginger extract | 10 | 10 | 28 | 7 | (31-37) |
| Group 4(Positive control) | Indomethacin | 0.5 | 0.5 | 28 | 7 | (41-47) |

5. Making of Adjuvant Arthritis Model

The solution (1.0 mg/0.1 mL) was made from 1 mL of FREUND'S INCOMPLETE ADJUTANT (FIA) and 10 mg of killed bacteria (fungus body)—MYCOBACTERIUM BUTYRICUM (Lot Ni. 5129117, Difco). The FIA and the killed bacteria were sufficiently suspended, and then approx.

1.1 mL of the solution was administered to the subcutaneous of the footpads of the right, hind leg of each mouse.

6. Observation Items and Observation Methods 6-1: Measurement of the Footpad Volume To verify the degree and the increase of the edema volume before and after the adjuvant was induced, the footpad volume of the right hind leg was measured by using Digital Pletysmometer, LE7500 (Panlab SL, Spain) twice each time immediately before the adjuvant was induced, and again on Days 3, 6, 10, 13, 17, 20, 24 and 27 after the adjuvant was induced.

6-2: Observation of the Articulation by X-Ray Picture

On the 27$^{th}$ day after the administration was begun, the edema was taken out. The hind leg was affixed with the neutral buffered formalin fixative (10%), and the image of the tarsus articulation area, including the interphalangeal articulation, was taken by a soft X-ray. The tarsus articulation and the interphalangeal articulation were verified by the degrees between −(normal status) and 5+(most serious status). A radiographic index was obtained by the method as shown in Chart 2, below. Add up the figures to determine the severity of the articular destruction.

CHART 2

Radiographic index.

| | | | Degree | | | |
|---|---|---|---|---|---|---|
| Item | Normal | Mild | Moderate (−) | Moderate (+) | Severe | Most severe |
| Periostitis | 0 | 1 | 2 | 3 | 4 | 5 |
| Bone destruction | 0 | 1 | 2 | 3 | 4 | 5 |

7. Statistical Processing

Each measured value was determined by Dunnet's Test using the Graphad Instat Program (Ver. 4.5, USA), and the significant difference test was conducted.

8. Result 8-1: Edema of the Tarsus Area

Chart 3 shows the volume of the right tarsus. As shown in the chart, below, the volume of the right tarsus area, before the edema was induced was 1.68 to 1.90 mL. On Day 3, it was 3.17 to 4.63 mL which is more than twice the volume before the edema was induced. It generally increased during the period between Days 6 and 24, and on Day 27, it slightly decreased. The comparison of each group's result shows that on Day 3, the average value of the vehicle (control) group was 4.14. The average value of the test substances, the red ginger extract (1 mg/kg) was 4.05, and the red ginger (10 mg/kg) was 3.75 mL, which showed that it slightly decreased, and the indomethacin (0.4 mg/kg) was 3.35 mL which showed the suppressing effect. On Day 24, the average value of the vehicle group was 5.01 mL. On the other hand, the test substance (1 mg/kg) was 4.98 mL, the test substance (10 mg/kg) was 4.02 mL, and the indomethacin (0.5 mg/kg) was 3.19 mL, which all slightly decreased. Thus, the average value of the test substance group (10 mg/kg) showed the suppressing effect.

CHART 3

Edema volume of the tarsus (mL)
Right tarsus (area where the adjuvant is administered)

| | | Group | | |
|---|---|---|---|---|
| Days | Control | Red ginger extract 1 mg/kg | Red ginger extract 10 mg/kg | Indomethacin 0.5 mg/kg |
| 0 | 1.82 ± 0.08 | 1.76 ± 0.08 | 1.82 ± 0.08 | 1.81 ± 0.07 |
| 3 | 4.14 ± 0.37 | 4.05 ± 0.41 | 3.75 ± 0.36 | 3.35 ± 0.18** |
| 6 | 4.82 ± 0.52 | 4.57 ± 0.74 | 4.33 ± 0.54 | 3.69 ± 0.40** |
| 10 | 4.82 ± 0.62 | 4.52 ± 0.69 | 4.28 ± 0.67 | 3.69 ± 0.36** |
| 13 | 4.75 ± 0.64 | 4.72 ± 0.72 | 3.95 ± 0.60* | 3.40 ± 0.43** |
| 17 | 4.76 ± 0.57 | 5.00 ± 1.30 | 4.19 ± 0.90 | 3.11 ± 0.59** |
| 20 | 4.80 ± 0.81 | 4.96 ± 1.40 | 4.04 ± 0.83 | 3.18 ± 0.52** |
| 24 | 5.01 ± 0.71 | 4.98 ± 1.44 | 4.02 ± 0.85 | 3.19 ± 0.51** |
| 27 | 4.59 ± 0.57 | 4.44 ± 1.74 | 3.84 ± 0.82 | 2.89 ± 0.34** |

Average value ± Standard error
Significant differences between the values marked with * or ** and the values of the Control group are $P < 0.05$ and $P < 0.01$ respectively.

Chart 4 shows the degree of severity in regard to the disorder of the right interphalangeal articulation.

CHART 4

X-ray determination on the right tarsus articulation area and interphalangeal articulation area

| | No. of mouse | Tarsus articulation | | | Interphalangeal articulation | | | Result |
|---|---|---|---|---|---|---|---|---|
| | | Periostitis | Bone destruction | Total | Periostitis | Bone destruction | Total | |
| control | 11 | 3+ | 2+ | 5 | + | 2+ | 3 | 3+ |
| | 12 | 4+ | 2+ | 6 | 3+ | + | 4 | 4+ |
| | 13 | 3+ | 3+ | 6 | 4+ | + | 5 | 3+ |
| | 14 | 5+ | 2+ | 7 | 4+ | + | 5 | 5+ |
| | 15 | 4+ | 2+ | 6 | 3+ | + | 4 | 4+ |
| | 16 | 4+ | 2+ | 6 | 2+ | + | 3 | 4+ |
| | 17 | 4+ | 2+ | 6 | 3+ | + | 4 | 4+ |
| Red ginger extract 1 mg/kg | 21 | 4+ | 2+ | 6 | 4+ | 2+ | 6 | 4+ |
| | 22 | 5+ | 2+ | 7 | 5+ | + | 6 | 5+ |
| | 23 | 3+ | 3+ | 6 | + | + | 2 | 3+ |
| | 24 | 3+ | 3+ | 6 | 2+ | + | 3 | 3+ |
| | 25 | 3+ | 2+ | 5 | − | − | 0 | 2+ |
| | 26 | 4+ | 2+ | 6 | 2+ | + | 3 | 4+ |
| | 27 | 3+ | 2+ | 5 | + | − | 1 | 3+ |
| Red ginger extract 10 mg/kg | 31 | 5+ | 3+ | 8 | + | + | 2 | 5+ |
| | 32 | 2+ | + | 3 | − | − | 0 | 2+ |
| | 33 | 4+ | 2+ | 6 | 2+ | + | 3 | 4+ |
| | 34 | 3+ | 3+ | 6 | + | 3+ | 4 | 2+ |
| | 35 | 4+ | 2+ | 6 | 2+ | − | 2 | 3+ |

CHART 4-continued

X-ray determination on the right tarsus articulation area
and interphal angeal articulation area

| | No. of mouse | Tarsus articulation | | | Interphal angeal articulation | | | Result |
|---|---|---|---|---|---|---|---|---|
| | | Periostitis | Bone destruction | Total | Periostitis | Bone destruction | Total | |
| Indomet hacin 0.5 mg/kg | 36 | 2+ | + | 3 | – | – | 0 | 2+ |
| | 37 | 4+ | 2+ | 6 | + | + | 2 | 3+ |
| | 41 | 2+ | – | 2 | + | – | 1 | 2+ |
| | 42 | 2+ | + | 3 | + | – | 1 | 2+ |
| | 43 | 2+ | – | 2 | + | – | 1 | 2+ |
| | 44 | 2+ | + | 3 | – | – | 0 | 2+ |
| | 45 | 2+ | + | 3 | + | – | 1 | 2+ |
| | 46 | 2+ | + | 3 | + | + | 2 | 2+ |
| | 47 | 3+ | + | 4 | + | – | 1 | 2+ |

Normal: –; 0 point,
Mild: +; 1 point,
Moderate(–): 2+; 2points,
Moderate(+): 3+; 3 ponts,
Severe: 4+; 4 points
Most severe 5+; 5 points In Chart 4, the test result of the control group shows that periostitis (3+ to 5+) and bone destruction (2+ and 3+) were verified in the tarsus articulation of all the examples (7 examples), and that periostitis (+ to 4+) and bone destruction (+ or 3+) were verified in the interphalangeal articulation in all the examples. Thus, the result indicated 3+ to 5+.

The result of the red ginger extract (1 mg/kg) shows that periostitis (3+ to 5+) and bone destruction (2+ and 3+) were verified in the tarsus articulation of all the examples (7 examples). No disorder was verified in the interphalangeal articulation of Sample No. 25. Six examples of periostitis (+ to 5+) and five examples of bone destruction (+ or 2+) were verified. Thus, the result indicated 2+ to 5+ and each figure varied depending on the sample. The degree of disorder was almost the same as that of the vehicle group.

The test result of the red ginger extract (10 mg/kg) shows that periostitis (2+ to 5+) and bone destruction (+ to 3+) were verified in the tarsus articulation of all the samples (7 samples). No disorder was verified in the interphalangeal articulation of Sample Nos. 32 and 36. Five examples of periostitis (+ or 2+) and four Examples of bone destruction (+ or 3+) were verified. The result indicates 2+ to 5+ and the figures varied depending on the Example. Disorder was slightly suppressed compared to that of the vehicle group.

The test result of indomethacin (0.5 mg/kg) shows that periostitis (2+ or 3+) was verified in the tarsus articulation of all the examples (7 examples), and bone destruction (+) was verified in five examples. No disorder was verified in the interphalangeal articulation of Sample No. 44. Six examples of periostitis (+) and one example of bone destruction were verified in the interphalangeal articulation of Sample No. 44, and six examples of periostitis (+) and one example of bone destruction (+) were verified in the interphalangeal articulation. The result indicated 2+. Disorder was remarkably suppressed compared to that of the vehicle group.

On the other hand, no bone disorder was verified in the left tarsus articulation. But several examples of sporadic and minor periostitis of the tarsus articulation were verified in each group, except in the group of indomethacin (0.5 mg/kg).

As shown in Chart 4, the edema is suppressed by the administration of the red ginger extract. The group of 10 mg/kg has a more suppressive effect than the group of 1 mg/kg, that is, it correlates with the dosage. The group of 10 mg/kg slightly suppresses the periostitis and bone destruction. Thus, it is clearly verified that the red ginger extract in Example 1 has the preventive effect and the treatment effect on rheumatic arthritis or the like.

Test Example 2

Preventive Effect on Collagen Arthritis

Test Animal

DBA/1 J Mouse (Male/5 Week Old)

Test Method

A mixed emulsion of equal parts of bovine collagen type II solution (Collagen Technical Laboratory) and Freund Complete Adjuvant was intracutaneously administered to the tail base of the mouse. Booster injections were performed in the same way after three weeks. Between the $4^{th}$ and $12^{th}$ day, the mice having the edema were divided into four groups so that the level of edema in each group was equal. A 5% gum arabic solution was orally administered to the mice in Group 1. Then, a 5 mg/kg, 10 mg/kg, and 20 mg/kg of the red ginger extract of Example 1 were orally administered once a day to the mice of Groups 2 to 4, respectively. Said emulsion was administered to the mice for a period of 31 days, and the level of edema was measured every three or four days. A Kruskal-Wallis test was conducted as the significant difference test. Also, the level of edema (arthritis severity score) is indicated by 5 stages as shown in the chart below, and the total scores (max. 16) of the both legs were evaluated.

Level of Edema:

'0' indicates normal status.

'1' indicates only skin flare or slight edema.

'2' indicates obvious edema or inflammation of digit.

'3' indicates bad edema with skin flare.

'4' indicated severe edema with heavy skin flare.

The result is shown in Chart 5 and FIG. 1

CHART 5

| | | | | | Days | | | | | |
|---|---|---|---|---|---|---|---|---|---|---|
| | 0 | 3 | 7 | 11 | 14 | 17 | 21 | 25 | 28 | 31 |
| Arthritis Severity Scores — Gum Arabic solution Control | 7.9 | 8.7 | 9 | 9 | 7.2 | 7.3 | 8 | 5.8 | 8.5 | 7.5 |
| Red ginger extract 5 mg/kg | 7.9 | 7.1 | 8.6 | 9.1 | 7 | 7 | 6.6 | 5.5 | 6.6 | 6.5 |
| Red ginger extract 10 mg/kg | 8.3 | 6.5 | 7 | 6 | 6.2 | 6 | 4.6 | 5 | 7.6 | 6 |
| Red ginger extract 20 mg/kg | 8.3 | 8.9 | 7.7 | 6.6 | 6.6 | 6 | 4.9 | 6.3 | 8 | 7.7 |

Result

As shown in Chart 5 and FIG. 1, the arthritis severity scores of the mice having the red ginger extract subsequently remain at low levels. The significant decrease of the arthritis severity scores can be seen in the group of the red ginger extract (10 mg/kg) on Days 11 and 21, and in the group of the red ginger extract (20 mg/kg) on Day 21, respectively, compared to the control group. According to the result, it is obvious that the oral administration of the red ginger extract suppressed the inflammation caused by arthritis. Therefore, the red ginger extract of Example 1 has the preventive and therapeutic effect on the rheumatic arthritis or the like.

Test Example 3

COX Inhibitory Activity

The test was conducted by using a COX Inhibitor Screening Assay kit (Cayman Chemical Corporate) according to the instruction manual attached to the kit. The results of COX-1 and COX-2 are shown in FIG. 2 and FIG. 3, respectively.
Result FIG. 2 shows that the red ginger extract at all concentrations promotes the activity of COX-1. On the other hand, FIG. 3 shows that the red ginger extract at all concentrations suppresses the activity of COX-2. Thus, it is verified that the red ginger extract of Example 1 at all concentrations selectively inhibits only the activity of COX-2. Therefore, the red ginger extract has the antipyretic and analgesic actions, as well as the action to reduce side effects, such as gastrointestinal disorder, kidney problems or the like. Furthermore, the red ginger extract has a preventive and therapeutic effect on rheumatic arthritis or the like.

Test Example 4

Writhing Model (Anti-Acute-Inflammatory Test)

The Whittle method was used. A sample was made by suspending the red ginger extract with 5% gum arabic. Doses of 10 mg/kg, 50 mg/kg and 100 mg/kg were orally administered to the mice, and after 55 minutes, 2% pontamine sky blue (10 mL/kg) was injected into the caudal vein. After 5 minutes, 1% acetic acid (10 mL/kg) was intraperitoneally administered to the mice. The number of writhings was recorded for 15 minutes after administrating the 1% acetic acid. The result is shown in FIG. 4.

Conduct ventrotomy to the mice 20 minutes after administrating the 2% pontamine sky blue. Then, clean well the abdominal cavity with 8 mL of normal saline solution. Filter the peritoneal washing through the absorbent cotton. Then add 0.1 mL of 1 N NaOH solution and normal saline solution until the total volume becomes 10 mL. Determine the absorbance at 590 nm. The result is shown in FIG. 5.
Result.

It was verified that the administration of the red ginger extract (10 mg/kg) significantly reduced the writhing compared to the control group (Inhibition ratio: 38.7%, $P<0.05$). It was also verified that the administration of the red ginger extract (50 mg/kg and 100 mg/kg) significantly inhibited the writhings (respective inhibition ratio: 44.1% and 58.0% $P<0.01$) (See FIG. 4). On the other hand, due to the vascular hyperpermeability action of acetic acid, the administration of the red ginger extract (10 mg/kg) reduced the leakage of pigment compared to the control group (Inhibition ratio: 25.5%, $P>0.05$). Also, the administration of the red ginger extract (50 mg/kg and 100 mg/kg) significantly inhibited the leakage of pigment (respective inhibit ratio: 51.9% and 50.1%, $P<0.05$). (See FIG. 5).

From the above result, the red ginger extract shows to have an analgesic effect and an anti-inflammatory effect against acute inflammation in a mouse which is induced with acetic acid. Therefore, it is verified that the red ginger extract of Example 1 can be used as an analgesic agent and as an antipyretic agent.

Test Example 5

Measurement of the Effect on the PGE2 Produced by LPS Stimulation in RAW264.7 Cells Test Example 5-1

Measurement of the Effect on the PGE2 Produced in RAW264.7 Cells in Regard to the Red Ginger Extract of Example 1

Suspend mouse-derived macrophage-like cells RAW264.7 in the culture medium "Minimum Essential Medium (MEM)" containing a 0.1 mM nonessential amino acid mixture, 10% fetal calf serum (FCS), penicillin (100 units/mL), and streptomycin (100 microgram/mL) in concentration of $1\times10^6$ cells/mL. Then, the cells were seeded into 48-well plate (200 microliter/well).

In 48 to 72 hours after the cultivation, vacuum the culture medium. Then clean the culture medium thrice with the serum-free culture medium (which contains no FCS). Then, add the serum-free culture medium (170 microliter) to each well.

After that, add the LPS solution (10 microlitre) which was prepared to 200 microgram/mL in the serum-free culture medium, to each well (final concentration 10 microgram/mL). Then, add the serum-free culture medium (10 microliter) to the well of the control group. Add 20 microliter each of the red ginger extract sample solution which was prepared to be the concentrations of 1, 3, 10, and 100 microgram/mL in the serum-free culture medium, and add indomethacin in concentration of 8.9 microgram/mL (equivalent to 25 microM) to three wells, each. (The final concentrations of the red ginger extract are to be 0.1, 0.3, 1, 3, and 10 microgram/mL, and the final concentration of indomethacin is to be 0.89microgram/mL which is equivalent to 2.5 microM). Add 20 microliter each of the serum-free medium to the wells of the control group.

After a 20-hour cultivation period, collect the culture supernatant. Then, measure the concentration of $PGE_2$ in the culture supernatant. The measurement of the $PGE_2$ was conducted according to the instruction manual attached to Prostaglandin E2 E1A Kit-Monoclonal. The result is shown in FIG. 6.

FIG. 6 shows that the red ginger extract in a concentration of 0.1 to 10 microgram/mL has the effect to suppress the $PGE_2$ produced by the LPS stimulation in RAW264.7 cells.

From the above result, it is verified that the red ginger extract suppresses the production of the inflammatory factor $PGE_2$. Therefore, it can be concluded that as one mechanism of the anti-inflammatory effect, the red ginger extract inhibits the activity of COX-2 and suppresses the production of $PGE_2$.

Test Example 5-2

Measurement of Effect of 6-Gingerol, Anthocyanin Fraction, or Mixture thereof on $PGE_2$ Produced in RAW264.7 Cells A 20 microliter sample solution (6-gingerol of Example 2-1: 7-anthocianin fracture of Example 2-7=10:1, 2:1, 1:1, 1:2, and 1:10) which was prepared in the serum-free culture medium, and a 20 microliter of 6-gingerol only and solution, a 20 microliter of anthocyanin fraction, only, were respectively added to 3 wells. A measurement was taken under the same condition as that of the above test Example 5-1 except one condition that the final concentrations of 6-gingerol of Example 2-1: 7-anthocyanin fraction of Example 2-7 are 0.1:0.01, 0.1:0.05, 0.1:0.1, 0.05:0.1, 0.01:0.1, 0.1:0, 0:0.1 microgram/mL. (This calculation is based on the use of pure anthocyanin). The result is shown in FIG. 7. The expressions "G0.1A0", "G0.1A0.01", "G0.1A0.05", "G0.1 A0.1", "A0.1G0.01", "A0.1G0.01", "A0.1G0.05, and "A0.1G0" mean the final concentrations of 6-gingerol of Example 2-1 to anthocyanin fraction of Example 2-7 are respectively 0.1:0", "0.1:0.01", "0.1:0.05", "0.1:0.1", "0.1:0.01", "0.1:0.01", "0.1:0.05, and "0.1:0" (This calculation is based on the use of pure anthocyanin).

FIG. 7 shows that a 6-gingerol only, or an anthocyanin fraction only, in a concentration of 0.1 microgram/mL, respectively, suppresses the $PGE_2$ produced by the LPS stimulation in RAW264.7 cells. (In both groups of 6-gingerol and anthocyanin fraction, P is less than 0.01 (P<0.01) compared to the LPS group, and the inhibition ratio is 37.8% and 54.9% respectively). Compared to the groups of 6-gingerol only and anthocyanin fraction only, the compound with a wide rage of proportion of 6-gingerol to anthocyanin fraction (i.e. 10:0 to 1:10) furthermore inhibits the $PGE_2$ produced in RAW264.7 cells. Probability (P values) of each group is less than 0.01 (P<0.01) compared to the groups of LPS, 6-gingerol and anthocyanin, and the inhibition ratio rises to 80%.

From the above results, it is verified that the 6-gingerol and the anthocyanin fraction inhibit the production of the inflammatory factor $PGE_2$. Therefore, the 6-gingerol and anthocyanin fraction have a synergetic effect to inhibit the inflammatory factor $PGE_2$ produced in RAW264.7 cells. The mixture of the 6-gingerol and anthocyanin fraction has a more inhibitory effect against the production of the inflammatory factor $PGE_2$ Test Example 6

Chemotaxis of Human Peripheral Blood-Derived Monocytes

Procedure.

Expose a monocyte fraction derived from human peripheral blood in the red ginger extract of Example 1 (Concentrations: 100, 33.3, 11.1, and 3.7 microgram/mL). Then, set it in the chemotaxis equipment (TAXIScan, Effector Cell Institute) to determine the number of amebocytes induced by the stimulation of the macrophage chemotactic factor (MCP-1). With the image data obtained in the above procedure, analyze the streaming of cells by TAXIScan Analyza. FIG. 8 shows the number of cells streaming per second in each determination. Also, in FIG. 8, the word "extract" means red ginger extract of Example 1.

As a result, it is verified that the number of streaming cells decreases when the concentration of the red ginger extract is high.

Therefore, it is also verified that the red ginger extract of Example 1 has a preventive effect on arthritis as well as on other kinds of chronic inflammation.

Test Example

NO Production Inhibition Test

Test Example 7-1

NO Production Inhibition Test on the Red Ginger Extract and its Components

A 200 microliter each of the continuously-cultivated RAW264.7 cells ($10^6$ cells/mL) should be seeded into 48-well plate. After 24 hours, replace the culture medium with a serum-free culture medium. Then, add the LPS (final concentration: 10 microgram/mL) and samples (Examples 1 & 2), and then cultivate for 24 hours. Collect the supernatant (100 microliter) and determine the amount of NO by the Griess Method. The result is shown in FIG. 6.

CHART 6

| Concentration (μg/mL) | 0 (LPS−) | 0 (LPS+) | 1 | 3 | 10 | 30 | 100 |
|---|---|---|---|---|---|---|---|
| Red ginger extract (Example 1) | 1.04 ± 0.20 | 4.11 ± 0.40 | 3.87 ± 0.34 (7.8) | 3.84 ± 0.23 (8.8) | 3.81 ± 0.30 (9.8) | 3.59 ± 0.26 (16.9) | 2.59 ± 0.29 (49.5) |
| 4-gingerol (Example 2-2) | 1.17 ± 0.18 | 4.77 ± 0.28 | 4.98 ± 0.22 | 5.10 ± 0.24 | 4.98 ± 0.22 | 5.03 ± 0.45 | 4.98 ± 0.26 |
| 6-gingerol (Example 2-1) | 0.96 ± 0.14 | 3.21 ± 0.27 | 3.50 ± 0.26 | 3.66 ± 0.33 | 3.27 ± 0.26 | 3.11 ± 0.22 (4.3) | 2.81 ± 0.47 (17.6) |
| 8-gingerol | 0.72 ± 0.18 | 4.34 ± 0.21 | 4.17 ± 0.27 | 4.06 ± 0.24 | 3.86 ± 0.32 | 3.59 ± 0.21 | 3.20 ± 0.17 |

CHART 6-continued

| Concentration (μg/mL) | 0 (LPS−) | 0 (LPS+) | 1 | 3 | 10 | 30 | 100 |
|---|---|---|---|---|---|---|---|
| (Example 2-3) | | | (4.7) | (7.7) | (13.3) | (20.7) | (31.5) |
| 10-gingerol | 1.12 ± 0.43 | 4.20 ± 0.17 | 4.44 ± 0.27 | 4.32 ± 0.16 | 4.33 ± 0.50 | 4.28 ± 0.72 | 3.55 ± 0.08 |
| (Example 2-4) | | | | | | | (21.1) |
| 6-shogaol | 0.98 ± 0.17 | 3.56 ± 0.30 | 3.81 ± 0.29 | 3.60 ± 0.29 | 3.21 ± 0.31 | 2.79 ± 0.09 | 1.22 ± 0.04 |
| (Example 2-5) | | | | | (13.6) | (29.8) | (90.7) |
| 10-shogaol | 1.21 ± 0.18 | 3.26 ± 0.64 | 2.78 ± 0.10 | 2.88 ± 0.11 | 2.76 ± 0.10 | 2.68 ± 0.70 | 2.62 ± 0.71 |
| (Example 2-6) | | | (23.4) | (18.5) | (24.4) | (28.3) | (31.2) |

Upper: NO in supernatant (μM)
Average value ± SD
Bottom: Inhibition ratio (%)

Chart 6 shows that the red ginger extract in concentration of 100 microliter/mL has an inhibitory effect on NO production. Also, it shows that the 6-shogaol has a comparatively strong effect among the ingredients. From the above result, it is verified that the red ginger extract and its component (especially, shogaol) inhibits the macrophage activity.

Test Example 7-2

NO Production Inhibition Test on Mixture of the Red Ginger Extract and Glucosamine Hydrochloride Procedure:

As a test sample, use glucosamine hydrochloride (Wako Pure Chemical Industries, Ltd.) and the red ginger extract of Example 1. Seed 200 microliter each of the continuously-cultivated RAW264.7 cells ($10^6$ cells/mL) into 48-well plate. After a 24-hour cultivation period, replace the culture medium with the serum-free culture medium containing two different samples which were prepared to become the same concentrations as shown in FIGS. 10 and 11. Then, cultivate it for 6 hours. After that, add the LPS (final concentration 10 microgram/mL) and the samples, and cultivate it for 24 hours. Collect the supernatant (100 microliter), and determine the amount of NO by the Griess Method. Also, the protocol of the sample processing refers to the cited reference "Meininger C. J. et al., Glucosamine inhibits inducible nitric oxide synthesis. Biochem. Biophs. Commun. 279, 234-239 (2000)". The graph indicating the inhibitory effect of glucosamine hydrochloride on NO production, which is disclosed in the above cited reference, is now shown in FIG. 9.

The relation between concentrations of the red ginger extract of Example 1 as a sample and the inhibitory effect on NO production is shown in FIG. 10. Furthermore, the relation between the mixture ratio of the red ginger extract and glucosamine hydrochloride as samples of Example 1 and the inhibitory effect on NO production is shown in FIG. 11.

Result

As shown in FIG. 9, it is reported that glucosamine hydrochloride in concentration of 21.5 to 215 microgram/mL has the inhibitory effect on NO production. On the other hand, the red ginger extract in concentration of 10 to 200 microgram/mL has the inhibitory effect on NO production (See FIG. 10). Glucosamine hydrochloride (100 microgram/mL), coexisted with the red ginger extract (10 microgram/mL), has a more significant inhibitory effect on NO production than the single substance of the glucosamine hydrochloride or the red ginger extract (See FIG. 11). However, when the concentration of the red ginger extract increases to 100 microgram/mL, the inhibitory effect of NO production decreases. From the above result in this test, it is verified that glucosamine and the red ginger extract in a mixture ratio of 10:1 has the synergetic inhibitory effect on NO production.

The blending samples of the anti-inflammatory agent (red ginger extract) in this invention are herein described without limitation.

Blending Sample 1: Chewing Gums

| | |
|---|---|
| Sugar: | 53.0 wt % |
| Gum base: | 20.0 |
| Glucose: | 10.0 |
| Starch syrup: | 16.0 |
| Aroma chemical: | 0.5 |
| Red ginger extract | 0.5 |
| | 100.0 wt % |

Blending Sample 2: Gummies

| | |
|---|---|
| Reduced starch syrup: | 40.0 wt % |
| Granulated sugar: | 20.0 |
| Glucose sugar: | 20.0 |
| Gelatin: | 4.7 |
| Water: | 9.68 |
| Kiwi fruit juice: | 4.0 |
| Kiwi fruit flavor: | 0.6 |
| Pigment: | 0.02 |
| Red ginger extract | 1.0 |
| | 100.0 wt % |

Blending Example 3: Candies

| | |
|---|---|
| Sugar: | 50.0 wt % |
| Starch syrup: | 33.0 |
| Water: | 14.4 |
| Organic acid: | 2.0 |
| Aroma chemical: | 0.2 |
| Red ginger extract: | 0.4 |
| | 100.0 wt % |

Blending Example 4: Yogurts (Natural/Firm)

| | |
|---|---|
| Milk: | 41.5 wt % |
| Skimmed milk: | 5.8 |
| Sugar: | 8.0 |
| Agar-agar: | 0.15 |
| Gelatin: | 0.1 |

-continued

| | |
|---|---|
| *Lactobacillus*: | 0.005 |
| Red ginger extract: | 0.4 |
| Aroma chemical: | Trace amount |
| Water: | Rest |
| | 100.0 wt % |

Blending Sample 5: Soft Drinks

| | |
|---|---|
| High fructose corn syrup: | 30.0 wt % |
| Emulsifying agent: | 0.5 |
| Red ginger extract: | 0.05 |
| Aroma chemical: | Appropriate amount |
| Distilled water: | Rest |
| | 100.0 wt % |

Blending Sample 6: Tablet-Shaped Sweets

| | |
|---|---|
| Sugar: | 76.4 wt % |
| Glucose: | 19.0 |
| Glycerin fatty acid ester: | 0.2 |
| Red ginger extract: | 0.5 |
| Distilled water: | 3.9 |
| | 100.0 wt % |

Blending Sample 7: Tablets

| | |
|---|---|
| Lactose: | 54.0 wt % |
| Crystalline cellulose: | 30.0 |
| Starch splitting product: | 10.0 |
| Glycerin fatty acid ester: | 5.0 |
| Red ginger extract: | 1.0 |
| | 100.0 wt % |

Blending Sample 8: Soft Capsules

| | |
|---|---|
| Red ginger oil: | 87.0 wt % |
| Emulsifying agent: | 12.0 |
| Red ginger extract: | 1.0 |
| | 100.0 wt % |

Blending Sample 9: Cosmetic Creams

| | |
|---|---|
| Squalene: | 20.0 wt % |
| Bees wax: | 5.0 |
| Distilled *jojoba* oil: | 5.0 |
| Glycerin: | 5.0 |
| Glycerin monostearate: | 2.0 |
| Polyoxyethylene (20) sorbitan-monostearate: | 2.0 |
| Red ginger extract: | 2.0 |
| Food preservative: | Appropriate amount |
| Aroma chemical: | Appropriate amount |
| Distilled water: | Rest |
| | 100.0 wt % |

Blending Example 10: Skin Lotions

| | |
|---|---|
| Ethanol: | 5.0 wt % |
| Glycerin: | 2.0 |
| 1,3-butylene glycol: | 2.0 |
| Polyethylene oleyl ether: | 0.5 |
| Sodium citrate: | 0.1 |
| Citric acid: | 0.1 |
| Red ginger extract: | 0.1 |
| Distilled water: | Rest |
| | 100.0 wt % |

Blending Example 11: Body Gel

| | |
|---|---|
| Macadamia nut oil: | 2.0 wt % |
| Octyl decyl myristate: | 10.0 |
| Methylphenyl polysiloxane: | 5.0 |
| Behenyl alcohol: | 3.0 |
| Stearic acid: | 3.0 |
| Batyl alcohol: | 1.0 |
| Glycel monostearate: | 1.0 |
| Tetra oleic acid polyoxyethylene sorbit: | 2.0 |
| Hydrogenated soybean phosphatide: | 1.0 |
| Ceramide: | 0.1 |
| Retinol palmitate: | 0.1 |
| Preservative: | Appropriate amount |
| Centella asiatica extract: | 1.0 |
| Red ginger extract: | 1.0 |
| 1,3-butylene glycol: | 5.0 |
| Distilled water: | Rest |
| | 100.0 wt % |

Blending Example 12: Cosmetic Emulsion

| | |
|---|---|
| Squalene: | 4.0 wt % |
| Vaseline: | 2.5 |
| Cetanol: | 2.0 |
| Glycerin: | 2.0 |
| Oleophilic glycerin monostearate: | 1.0 |
| Stearic acid: | 1.0 |
| L-arginine: | 1.0 |
| Red ginger extract: | 0.5 |
| Potassium hydroxide: | 0.1 |
| Aroma chemical: | Trace amount |
| Distilled water: | Rest |
| | 100.0 wt % |

Blending Example 13: Bath Agent (Liquid Type)

| | |
|---|---|
| Propylene glycol: | 50.0 wt % |
| Ethanol: | 20.0 |
| Sodium sulphate: | 5.0 |
| Red ginger extract: | 0.5 |
| Lanoline: | 0.5 |
| Avocado oil agent: | 0.5 |
| Pigment: | 1.5 |
| Aroma chemical: | 22.0 |
| | 100.0 wt % |

INDUSTRIAL APPLICABILITY

As described above, the anti-inhibitory agent or the like in this invention can be used for the prevention or treatment of rheumatic arthritis or the like, and also reduces the side effects, e.g. gastrointestinal disorders, kidney problems, or the like.

Figure 1:
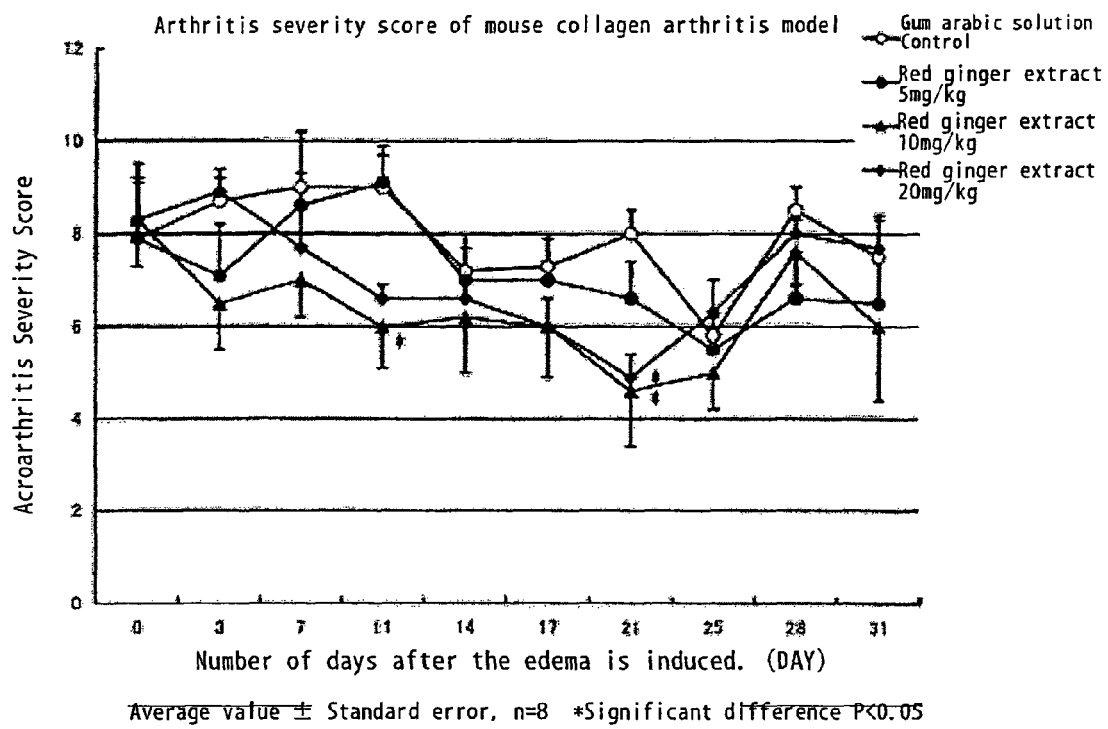
FIG. 1 is a graph showing the preventive effect of the red ginger extract of Example 1 on collagen arthritis.
Figure 2:
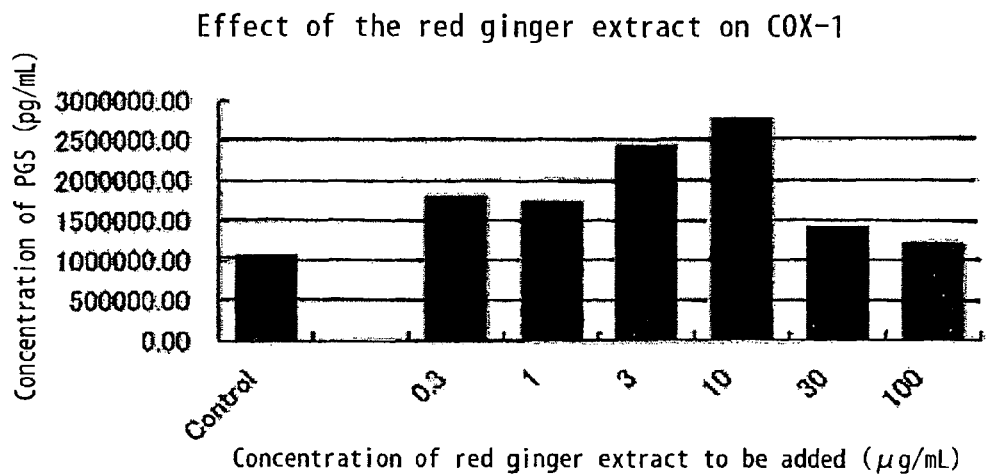
FIG. 2 is a graph showing the influence of the red ginger extract of Example 1 on a COX-1.
Figure 3:
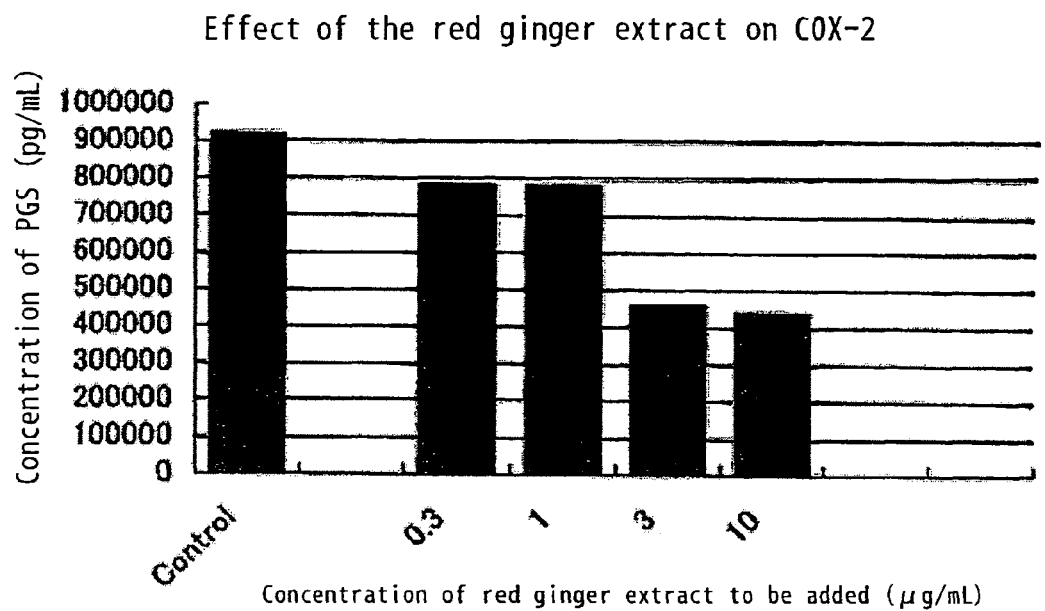
FIG. 3 is a graph showing the influence of the red ginger extract of Example 1 on a COX-2.
Figure 4:
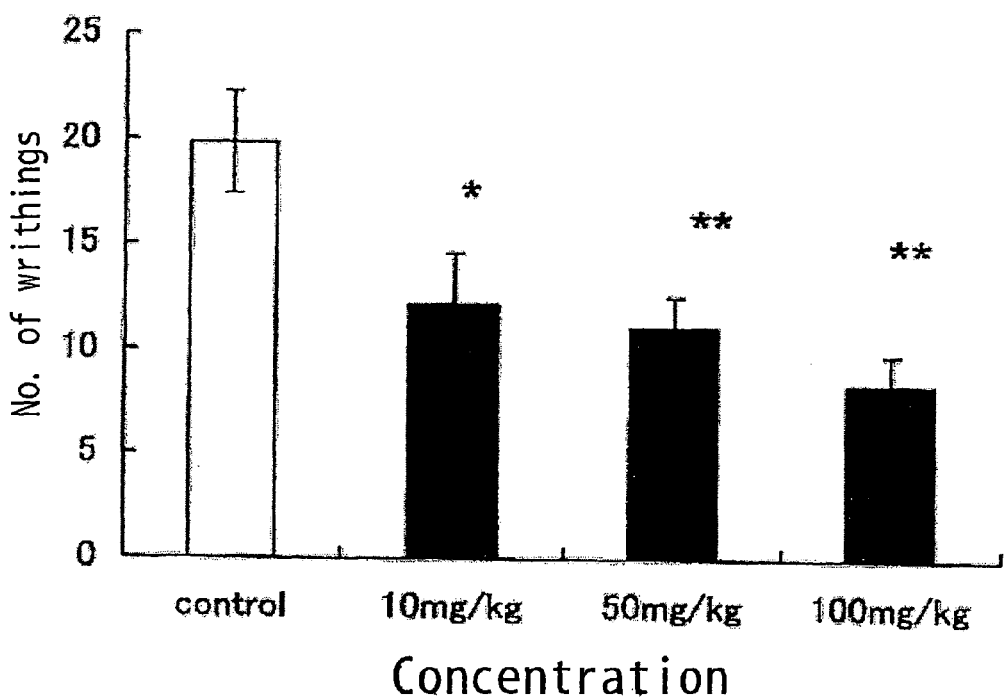
FIG. 4 is a graph showing the relation between the red ginger extract of Example 1 and the number of writhings for 15 minutes after administrating 1% acetic acid in the writhing model.
Figure 5:
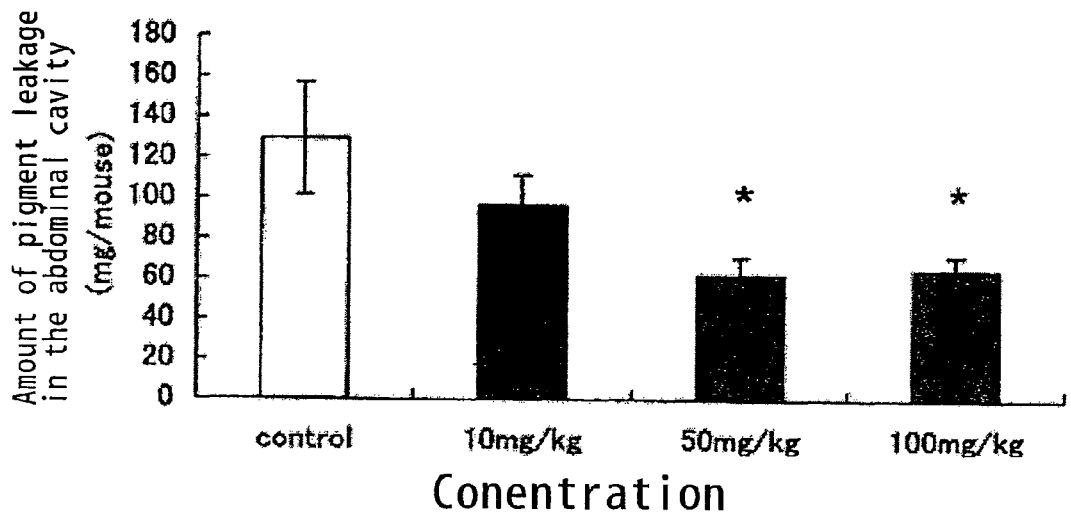
FIG. 5 is a graph showing the relation between the red ginger extract of Example 1 and the amount of leakage of pigment into the abdominal cavity in the writhing model.
Figure 6:
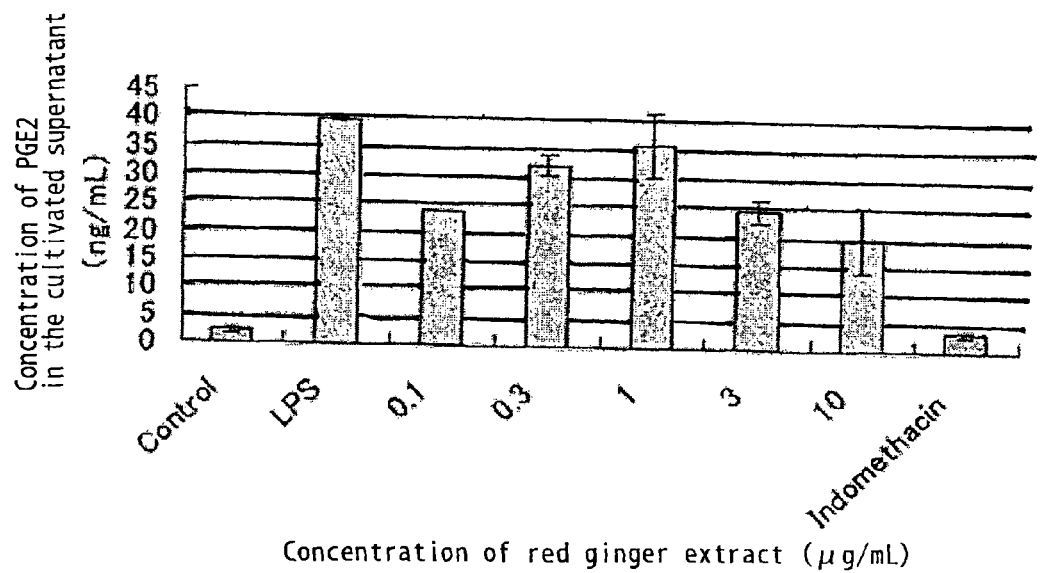
FIG. 6 is a graph showing the inhibitory activity of the red ginger extract of Example 1 on PGE2 production by the LPS stimulation in RAW26.7 cells.
Figure 7:
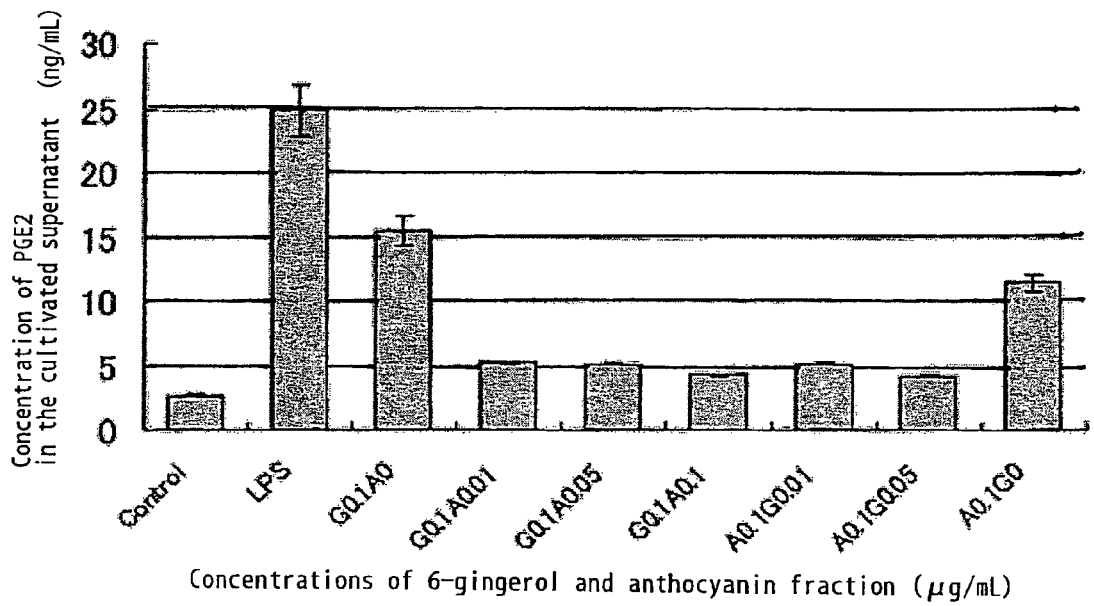
FIG. 7 is a graph showing the inhibitory activity of 6-gingerol, the anthocyanin fraction, and the mixture thereof of Example 2 on PGE2 production by the LPS stimulation in RAW26.7 cells.
Figure 8:
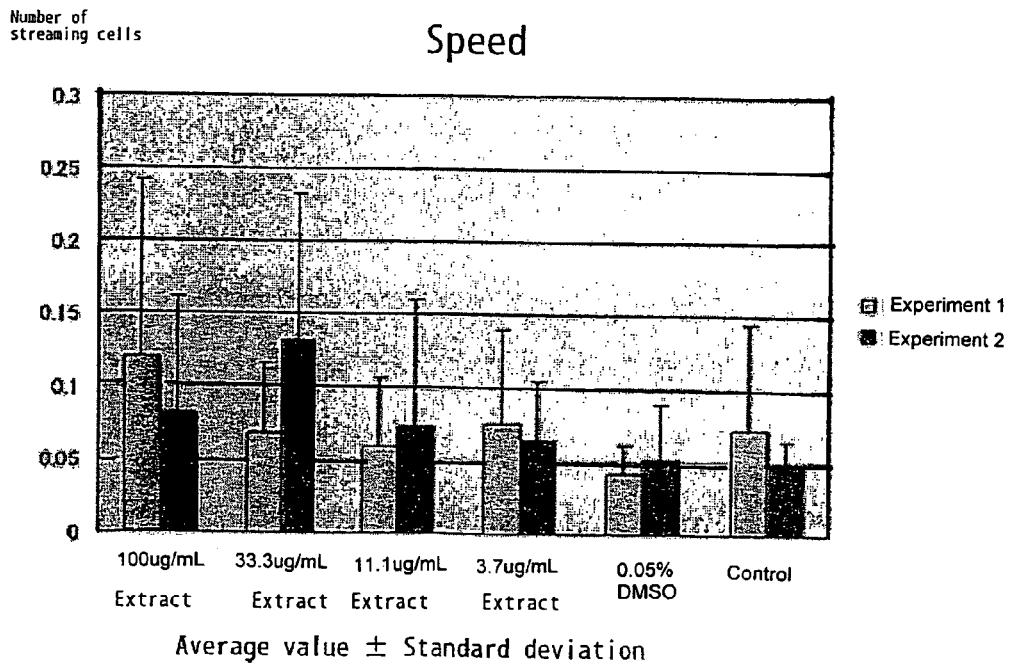
FIG. 8 is a graph showing the relation between the red ginger extract in various concentrations and number of the streaming cells per second induced by the MCP-1 stimulation to the human peripheral blood-derived monocytes.
Figure 9:
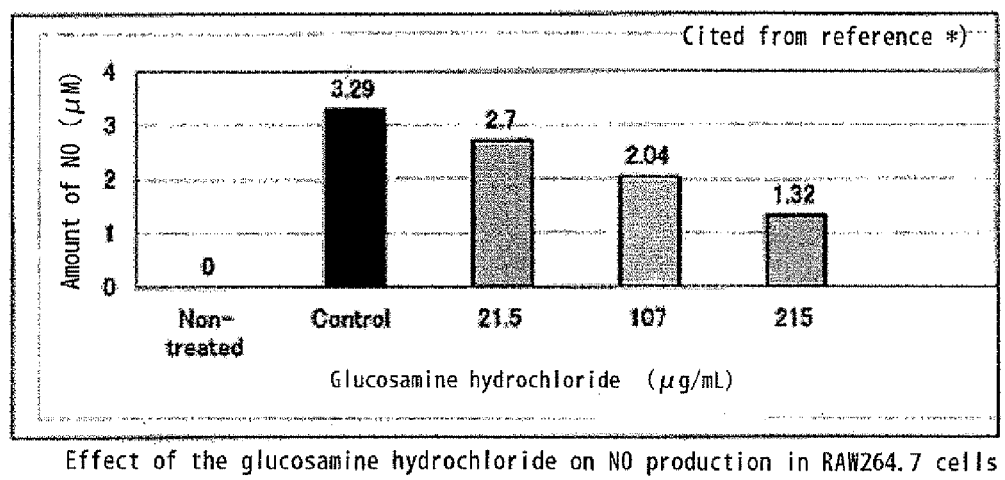
FIG. 9 is a graph showing the inhibitory effect of the glucosamine hydrochloride on NO production.
Figure 10:
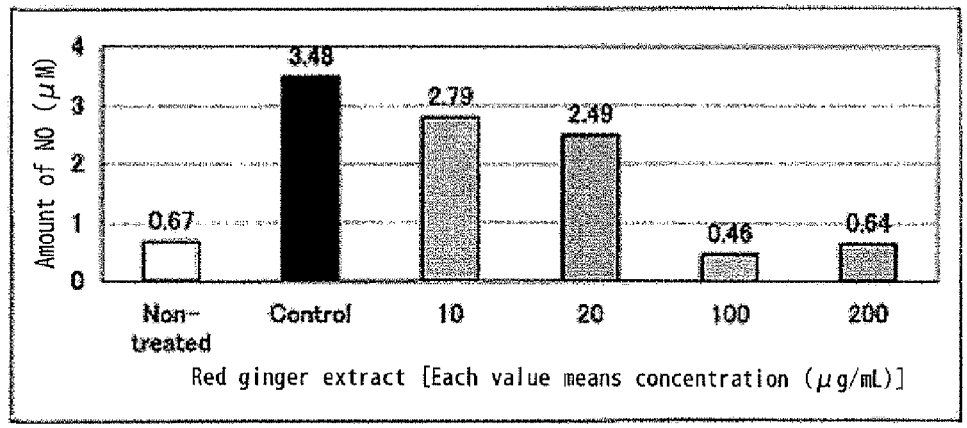
FIG. 10 is a graph showing the inhibitory effect of the red ginger extract of Example 1 on NO production.
Figure 11:
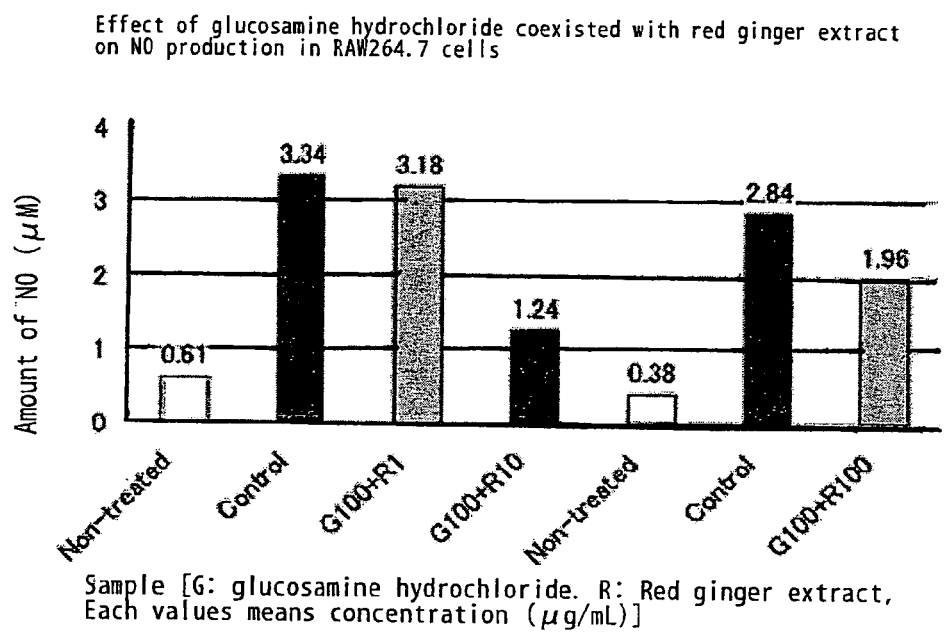
FIG. 11 is a graph showing the inhibitory effect of the red ginger extract of Example 1 and the mixture of the glucosamine hydrochloride on NO production.

What is claimed is:

1. A composition for inhibiting inflammation, said composition comprising 1 part by weight of red ginger (*Zingiber officinale*) extract comprising anthocyanidin and gingerol, and 10 parts by weight of glucosamine and/or its salt, wherein the red ginger extract is produced by the following method:
    a) extracting red ginger with n-hexane to obtain defatted red ginger,
    b) extracting the defatted red ginger of part (a) with hydrous ethanol,
    c) drying the hydrous ethanol extract of part (b) to remove the hydrous ethanol, and
    d) recovering the dried product remaining after the removal of hydrous ethanol of part (c), whereby the dried product is the red ginger extract.

2. A medicine comprising the composition according to claim 1, wherein said medicine is in the form of a tablet, a pill, a soft or hard capsule, a powder, a liquid, a skin patch, a lotion, an ointment or a cream.

3. A food comprising the composition according to claim 1.

4. The composition of claim 1, wherein said composition inhibits COX-2.

5. The composition of claim 1, further comprising a shogaol.

* * * * *